(12) United States Patent
Bachawala

(10) Patent No.: US 11,007,501 B2
(45) Date of Patent: May 18, 2021

(54) REDUCED PERMEABILITY MICROCAPSULES

(71) Applicant: Trucapsol LLC, Bethlehem, PA (US)

(72) Inventor: Praveen Bachawala, Allentown, PA (US)

(73) Assignee: Trucapsol LLC, Bethlehem, PA (US)

( * ) Notice: Subject to any disclaimer, the term of this patent is extended or adjusted under 35 U.S.C. 154(b) by 0 days.

(21) Appl. No.: 16/282,993

(22) Filed: Feb. 22, 2019

(65) Prior Publication Data

US 2019/0275490 A1    Sep. 12, 2019

Related U.S. Application Data

(60) Provisional application No. 62/639,943, filed on Mar. 7, 2018.

(51) Int. Cl.
*B01J 13/16* (2006.01)
*B23Q 16/02* (2006.01)
(Continued)

(52) U.S. Cl.
CPC ............. *B01J 13/16* (2013.01); *A01N 25/28* (2013.01); *A23L 27/72* (2016.08); *A61K 8/11* (2013.01);
(Continued)

(58) Field of Classification Search
None
See application file for complete search history.

(56) References Cited

U.S. PATENT DOCUMENTS 3,345,358 A    10/1967   Inklaar
3,819,838 A    6/1974    Smith et al.
(Continued)

FOREIGN PATENT DOCUMENTS

EP    0815743 A2    1/1998
EP    1371410 A1    12/2003
(Continued)

OTHER PUBLICATIONS

International Search Report and Written Opinion for PCT/US2019/018959 dated Jul. 8, 2019.
(Continued)

*Primary Examiner* — Sin J Lee
(74) *Attorney, Agent, or Firm* — Caesar Rivise, PC

(57) ABSTRACT

Disclosed is a composition including controlled release particles, wherein each of the controlled release particles includes: (a) a core including at least one hydrophobic active ingredient; and (b) a wall at least partially surrounding the core and including: (i) an outer layer including a copolymer of polyacrylamide and polyacrylate; (ii) an intermediate layer under the outer layer and including a polyurea; (iii) an inner layer under the intermediate layer and including an acrylate copolymer; and optionally (iv) an optional outer layer above the outer layer and including a quaternary amine containing moiety, wherein the inner layer is a mesh and the controlled release particles are effective to retain the at least one hydrophobic active ingredient upon exposure to water and effective to release the at least one hydrophobic active ingredient in response to friction. A method for preparing the composition is also disclosed.

17 Claims, 4 Drawing Sheets

(51) Int. Cl.

| | |
|---|---|
| *A61K 9/50* | (2006.01) |
| *A61K 8/11* | (2006.01) |
| *A23L 27/00* | (2016.01) |
| *A01N 25/28* | (2006.01) |
| *C11D 3/37* | (2006.01) |
| *C11D 3/50* | (2006.01) |
| *C11D 17/00* | (2006.01) |
| *F28D 20/02* | (2006.01) |

(52) U.S. Cl.
CPC .......... *A61K 9/5026* (2013.01); *A61K 9/5031* (2013.01); *A61K 9/5073* (2013.01); *B23Q 16/02* (2013.01); *C11D 3/3719* (2013.01); *C11D 3/3726* (2013.01); *C11D 3/3769* (2013.01); *C11D 3/505* (2013.01); *C11D 17/0039* (2013.01); *A61K 2800/412* (2013.01); *A61K 2800/56* (2013.01); *A61K 2800/805* (2013.01); *F28D 20/023* (2013.01)

(56) References Cited

U.S. PATENT DOCUMENTS

| | | |
|---|---|---|
| 5,550,189 A | 8/1996 | Qin et al. |
| 5,574,179 A | 11/1996 | Wahl et al. |
| 5,601,760 A | 2/1997 | Rosenberg |
| 6,248,909 B1 | 6/2001 | Akimoto et al. |
| 6,572,919 B2 | 6/2003 | Westland et al. |
| 7,431,986 B2 | 10/2008 | Van Lengerich et al. |
| 8,900,492 B2 | 12/2014 | Pacorel et al. |
| 9,205,395 B2 | 12/2015 | Yan |
| 9,332,774 B2 | 5/2016 | Nakhasi et al. |
| 9,937,477 B2 | 4/2018 | Zhang et al. |
| 9,993,401 B2 * | 6/2018 | Barnett .................. A61K 8/11 |
| 10,188,593 B2 | 1/2019 | Dihora et al. |
| 2004/0033264 A1 | 2/2004 | Sawhney |
| 2005/0272628 A1 | 12/2005 | Meli et al. |
| 2005/0276831 A1 | 12/2005 | Dihora et al. |
| 2008/0167188 A1 | 7/2008 | Fischer et al. |
| 2009/0209661 A1 | 8/2009 | Somerville Roberts et al. |
| 2011/0268778 A1 | 11/2011 | Dihora et al. |
| 2011/0268802 A1 | 11/2011 | Dihora et al. |
| 2012/0128752 A1 | 5/2012 | Loo et al. |
| 2013/0004617 A1 | 1/2013 | Zhang et al. |
| 2013/0022654 A1 | 1/2013 | Deshmukh et al. |
| 2013/0239429 A1 | 9/2013 | Vella et al. |
| 2014/0199244 A1 | 7/2014 | Rijcken et al. |
| 2014/0335032 A1 | 11/2014 | Panandiker et al. |
| 2015/0252312 A1 * | 9/2015 | de Villeneuve .... C11D 17/0039 510/515 |
| 2016/0038428 A1 | 2/2016 | Harel et al. |
| 2016/0128944 A1 | 5/2016 | Chawrai et al. |
| 2016/0158121 A1 * | 6/2016 | Lei ......................... C11D 3/505 424/401 |
| 2016/0166480 A1 | 6/2016 | Lei et al. |
| 2016/0206561 A1 | 7/2016 | Kohane et al. |
| 2016/0228338 A9 | 8/2016 | Dihora et al. |
| 2017/0165627 A1 | 6/2017 | Duan et al. |
| 2018/0015009 A1 | 1/2018 | Soubiran et al. |
| 2018/0042825 A1 | 2/2018 | Lei et al. |

FOREIGN PATENT DOCUMENTS

| | | |
|---|---|---|
| EP | 1797946 A2 | 6/2007 |
| WO | 9901214 A1 | 1/1999 |
| WO | 0105926 A1 | 1/2001 |
| WO | 03013538 A1 | 2/2003 |
| WO | 2006024411 A2 | 3/2006 |
| WO | 2007135583 A2 | 11/2007 |
| WO | 2009098226 A1 | 8/2009 |
| WO | 2016071151 A1 | 5/2016 |
| WO | 2017023830 A1 | 2/2017 |

OTHER PUBLICATIONS

Luo et al., "Zein-Based Micro- and Nano-Particles for Drug and Nutrient Delivery: A Review", J. Appl. Polym. Sci., vol. 40696, 12 pages (2014).

International Search Report for PCT/US2017/037855, dated Nov. 2, 2017.

Ko, Y. C., Ratner, B. D., & Hoffman, A. S. (1981). Characterization of hydrophilic-hydrophobic polymeric surfaces by aontact angle measurements. Journal of Colloid and Interface Science, 82(1), 25-37.

Polymer Properties Database. (n.d.). Retrieved Jul. 15, 2020, from http://polymerdatabase.com/polymer physics/sigma.html.

Adhesive and Sealant Council. (n.d.). Surface Energy and Wetting. adhesives.org & sealants.org. Retrieved Jul. 15, 2020, from https://www.adhesives.org/adhesives-sealants/adhesives-sealants-overview/structural-design/surface-energy-and-wetting.

* cited by examiner

REDUCED PERMEABILITY MICROCAPSULES

CROSS-REFERENCE TO RELATED APPLICATIONS

This application is a non-provisional of U.S. Application No. 62/639,943, filed Mar. 7, 2018, the contents of which are incorporated by reference herein in their entireties.

BACKGROUND OF THE INVENTION

1. Field of Invention

This invention relates to controlled release compositions, encapsulation compositions and methods for making and using them.

2. Description of Related Art

There are many microencapsulated delivery systems disclosed in the art to control the release of the encapsulated active, or provide release when a specific trigger is applied. Such systems have previously suffered from a number of drawbacks.

Controlled release microcapsules that provide release of active upon application of shear or friction generally suffer from several drawbacks: (1) such microcapsules cannot be formulated in certain classes of products due to strict formulation limits, (2) they have high permeabilities when incorporated into products that contain high levels of surfactant, solvents, and/or water, which results in the premature benefit agent release, (3) they can only effectively encapsulate a limited breadth of benefit agents, and (4) they either are so stable that they do not release the benefit agent in use or have insufficient mechanical stability to withstand the processes required to incorporate them in and/or make a consumer product and (5) they do not adequately deposit on the surface that is being treated with consumer product that contains capsules.

Such microcapsules are made via chemical processes that require the development of a membrane at the oil-water interface. Said membrane can be developed from the oil side or the water side, or both. An emulsion comprising the active material (dispersed phase) is stabilized in a continuous phase. In one mode, a shell material is deposited from the continuous phase onto a dispersed phase via precipitation of the shell material. In another mode, the shell material is manufactured within the dispersed phase, and migration of the shell material is induced via an interfacial reaction or insolubility of the shell material in the oil phase. The two approaches could be combined to develop "dual shell" capsules.

The permeability and the solubility parameter of this membrane determines the likelihood and the rate of diffusion of the encapsulated active out of the microcapsule. The solubility parameter of the membrane is determined by the choice of monomers that are reacted to form the shell material at the interface. The permeability of such shell material is determined by the crosslink density of the membrane. Polymers that are used to develop a membrane around the active material need to be crosslinked to provide a sufficient barrier to retain the encapsulated active until its desired release.

Chemical processes utilized to manufacture controlled release microcapsules generally utilize thermal initiators—either in the aqueous phase or the lipophilic phase. High crosslink density of the shell material can be achieved at higher temperatures, for two reasons. First, there is a higher reactivity of the monomers at high temperature. Second, as the monomers react, the resulting polymer has a higher glass transition temperature. A higher reaction temperature results in higher mobility of the crosslinked polymer, providing a means to achieve a higher reactivity of the monomers to achieve a higher crosslink density. However, controlled release microcapsules disclosed in the art are made in aqueous suspensions. Such capsule suspension can result in large losses of volatile actives when the aqueous suspension is taken to boiling temperatures, akin to a chemical distillation operation. The reaction temperatures to achieve a highly crosslinked density of the shell are generally limited to operating temperatures less than the boiling temperature of water. Such thermally initiated reactions require long batch cycle times due to the slow reaction kinetics at low temperatures. The ability to subject the capsules to reaction temperatures above 100° C. can increase the crosslink density of the particles and reduce permeability of the membrane.

Conventional controlled release particles that comprise a core and a shell have several limitations. First, such capsules prematurely release the active material when suspended in finished product formulations, such as cleaning product formulations. Second, the encapsulated active material is not released unless friction or shear is applied to break the microcapsule. Third, the encapsulated material in the core is often a pool of liquid that pours out of the microcapsule and is absorbed by the surrounding substrate. Such absorption is undesired especially when the encapsulated active is a volatile material that is desired to be released into the surrounding environment. Such absorption is also undesired when it is desired to control the release of the active from the microcapsule over a long duration of time. Fourth, such microcapsules have poor active delivery efficiency, since some of the microcapsules may never fracture to release the encapsulated active. For example, the fracture strength of particles is inversely proportional to the size of the microcapsule. That is, smaller particles are much more difficult to fracture than larger particles. Larger particles have much larger volume of active material than smaller particles. That is, fracturing a particle that has twice the radius of a comparative particle, results in 8 times the volume of active material released. Fifth, poor adhesion of particles to the substrate results in significant loss of the particles, especially when formulations containing such particles are used in rinse-off applications.

It is an object of the invention to provide microcapsules that have lower permeability. This is accomplished in two ways. First, multiple membranes are developed around the core material to reduce the diffusion, and seal the pores. Second, the core is transformed from a low viscosity liquid material, that can pour out of the microcapsule upon fracture, into a high viscosity semisolid mesh that retains the active material and controls the release of that active material over a duration of time.

It is an object of the invention to improve the adhesion of particles to substrates in rinse-off applications. Examples of such applications include laundering fabrics, shampooing hair, conditioning hair, cleansing the skin, showering, and the like. In such applications, a composition comprising microcapsules is applied to a substrate to initiate cleaning, and subsequently the composition is removed by using water. It is desired to remove soil and dirt, but also desired to retain active materials during the rinsing process. In such applications, the retention of microcapsules on the substrate is primarily accomplished via filtration. The present invention adheres such microcapsules onto desired substrates via the use of viscoelastic and electrostatic interactions. By adhering large particles as well as small particles during the rinse off application, the present invention delivers more volume of active material, and therefore a higher delivery efficiency of the encapsulated active. Conventional capsules are limited to the deposition of small particles, which carry much less volume of active material. Only a fraction of these small microcapsules fracture during use, resulting in significantly lower delivery efficiency of the encapsulated active. Moreover, the fracture of larger particles during the rinse-off application delivers a bloom of active material. Since the core material is a semisolid, such bloom of active material is delivered over a longer duration of time.

In order to deliver a consumer noticeable benefit, yet deliver that benefit at a low cost, encapsulation is used to isolate a uniquely different fragrance or flavor active from the non-encapsulated fragrance or flavor that is incorporated into the formulation. Acclamation to a flavor or fragrance requires a much higher concentration of the same fragrance or flavor to achieve noticeability. The invention allows one to encapsulate a uniquely different fragrance or flavor to incorporate into the composition, and achieve noticeability at significantly lower concentrations of the encapsulated active.

Hence, it is desired to provide low permeability microcapsules that are able to retain the encapsulated active in surfactant containing solutions, or under highly dilute aqueous conditions. It is further desired to improve the adhesion of microcapsules onto the desired substrate during rinse-off applications. It is still further desired to release the encapsulated active in larger quantities, and over a longer duration of time.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

A first aspect of the invention is a composition comprising controlled release particles, wherein each of the controlled release particles comprises:
(a) a core comprising at least one hydrophobic active ingredient; and
(b) a wall at least partially surrounding the core and comprising:
  (i) an outer layer comprising a copolymer of polyacrylamide and polyacrylate;
  (ii) an intermediate layer under the outer layer and comprising a polyurea;
  (iii) an inner layer under the intermediate layer and comprising an acrylate copolymer; and optionally
  (iv) an optional outer layer above the outer layer and comprising a quaternary amine containing moiety,
wherein the inner layer is a mesh and the controlled release particles are effective to retain the at least one hydrophobic active ingredient upon exposure to water and effective to release the at least one hydrophobic active ingredient in response to friction.

In certain embodiments, the composition is an aqueous suspension of the controlled release particles, wherein the controlled release particles are formed from a mixture comprising 18-40 wt. % of the at least one hydrophobic active ingredient, 0.55-9.3 wt. % of a urethane-acrylate oligomer, 0.15-2.6 wt. % of an amine, 0.2-3 wt. % of at least one acrylamide, 0.2-3.8 wt. % of at least one initiator, 0.2-3.2 wt. % of at least one water dispersible acrylate, 1.5-8.6 wt. % of a water soluble emulsifier and 50-56 wt. % water.

In certain embodiments, the composition is an agglomerate of the controlled release particles, wherein the controlled release particles are formed from a mixture comprising 18-40 wt. % of the at least one hydrophobic active ingredient, 0.55-9.3 wt. % of a urethane-acrylate oligomer, 0.15-2.6 wt. % of an amine, 0.2-3 wt. % of at least one acrylamide, 0.2-3.8 wt. % of at least one initiator, 0.2-3.2 wt. % of at least one water dispersible acrylate, 1.5-8.6 wt. % of a water soluble emulsifier and 50-56 wt. % water, and the agglomerate is formed by combining an aqueous suspension of the controlled release particles with at least one member selected from the group consisting of silicas, citric acid, sodium carbonate, sodium sulfate, sodium chloride, and binders.

In certain embodiments, the composition is a dry powder formed by dehydrating an aqueous suspension of the controlled release particles, wherein the controlled release particles are formed from a mixture comprising 18-40 wt. % of the at least one hydrophobic active ingredient, 0.55-9.3 wt. % of a urethane-acrylate oligomer, 0.15-2.6 wt. % of an amine, 0.2-3 wt. % of at least one acrylamide, 0.2-3.8 wt. % of at least one initiator, 0.2-3.2 wt. % of at least one water dispersible acrylate, 1.5-8.6 wt. % of a water soluble emulsifier and 50-56 wt. % water. In some of these embodiments, the dry powder comprises 31-62 wt. % of the at least one hydrophobic active ingredient, 0.9-16 wt. % of the urethane-acrylate oligomer, 0.2-4.4 wt. % of the amine, 0.3-5 wt. % of the at least one acrylamide, 10-23 wt. % of a polysaccharide, 0.35-6.5 wt. % of the at least one initiator, 0.3-5.5 wt. % of the at least one water dispersible acrylate, 2.5-13.5 wt. % of the water soluble emulsifier, 0-1.5 wt. % of a deposition aid, 0.5-1.0 wt. % silica, and optionally 0.10-1.5 wt. % of a desiccant.

In certain embodiments, the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the urethane-acrylate oligomer comprises acrylate and isocyanate functionalities, an isocyanate content from about 5 wt. % to about 15 wt. %, and an acrylate content from about 20 wt. % to about 50 wt. %.

In certain embodiments, the at least one water dispersible acrylate is a member selected from the group consisting of allyl methacrylate, triethylene glycol dimethacrylate, ethylene glycol dimethacrylate, diethylene glycol dimethacrylate, aliphatic urethane diacrylates, aromatic urethane diacrylates, difunctional urethane acrylates, ethoxylated aliphatic difunctional urethane methacrylates, aliphatic urethane dimethacrylates, aromatic urethane dimethacrylates, epoxy acrylates, epoxymethacrylates, tetraethylene glycol dimethacrylate, polyethylene glycol dimethacrylate, 1.3 butylene glycol diacrylate, 1,4-butanediol dimethacrylate, 1,4-butaneidiol diacrylate, diethylene glycol diacrylate, 1.6 hexanediol diacrylate, 1.6 hexanediol dimethacrylate, neopentylglycol diacrylate, polyethylene glycol diacrylate, tetraethylene glycol diacrylate, triethylene glycol diacrylate, 1.3 butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, ethoxylated trimethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate.

In certain embodiments, the amine is a member selected from the group consisting of lysine hydrochloride, urea, tryptophan hydrochloride, guanidine hydrochloride, aniline, cyanamide, 4-aminobenzoic acid, ethylenediamine, diethylenetriamine, guanidine and Girard's reagent.

In certain embodiments, the at least one acrylamide is an alkylidene-bis-acrylamide where the alkylidene group has up to four carbon atoms.

In certain embodiments, the at least one initiator used for polymerization is a member selected from the group consisting of peroxide, dialkyl peroxide, alkyl peroxide, peroxyester, peroxycarbonate, peroxyketone, peroxydicarbonate, 2,2'-azobis (isobutylnitrile), 2,2'-azobis(2,4-dimethylpentanenitrile), 2,2'-azobis(2,4-dimethylvaleronitrile), 2,2'-azobis(2-methylpropanenitrile), 2,2'-azobis(methylbutyronitrile), 1,1'-azobis(cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl) peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di t-amyl peroxide, 2,5-dimethyl-2, 5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate and ethyl 3,3-di-(t-amylperoxy)-butyrate.

In certain embodiments, the emulsifier is cationic or nonionic.

In certain embodiments, the emulsifier is selected from the group consisting of palmitamidopropyltrimonium chloride, distearyl dimonium chloride, cetyltrimethy lammonium chloride, quaternary ammonium compounds, fatty amines, aliphatic ammonium halides, alkyldimethyl benzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethyl aminoethyl methacrylate), poly(acrylamide-co-diallyldimethylammonium chloride), poly (allylamine), polybis(2-chloroethyl)ether-alt-1,3-bis(3-(dimethylamino)propylurea quaternized, poly (dimethylamine-co-epichlorohydrin-co-ethylenediamine), polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, partially hydrolyzed polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene), polyvinyl pyrrolidone, copolymers of polyvinhyl pyrrolidone, vinyl acetate and gum arabic.

In certain embodiments, the silica is a member selected from the group consisting of fumed silica, precipitated silica, calcium silicate, aluminosilicate, and combinations thereof.

In certain embodiments, the polysaccharide is a member selected from the group consisting of octenyl succinic acid anhydride modified starch, gum arabic, xanthan gum, gellan gum, pectin gum, konjac gum and carboxyalkyl cellulose.

In certain embodiments, the deposition aid is a member selected from the group consisting of poly(diallyl dimethylammonium) halides, copolymers of poly(diallyl dimethylammonium) chloride and polyvinyl pyrrolidone, acryl amides, imidazoles, imidazolinium halides, polyvinyl amine, copolymers of polyvinyl amine and N-vinyl formamide, polyvinylformamide, copolymers of polyvinylamine and polvyinylalcohol oligimers of amines, diethylenetriamine, ethylene diamine, bis(3-aminopropyl)piperazine, N,N-bis-(3-aminopropyl)methylamine, tris(2-aminoethyl) amine, polyethyleneimime, derivatized polyethyleneimine, ethoxylated polyethyleneimine, diester quaternary ammonium surfactants, diester quats combined with laminate nanoclays, polybutadiene/styrene, polybutadiene/acrylonitrile, carboxyl-terminated polybutadiene/acrylonitrile, chitosan with various degrees of deacetylation, carboxymethyl chitosans, glycol chitosans, whey protein, sodium caseinate, silk protein, polyamines and mixtures thereof.

In certain embodiments, the aqueous suspension comprises at least one processing aid selected from the group consisting of water, aggregate inhibiting materials and particle suspending polymers.

In certain embodiments, the controlled release particles have a diameter from 0.1 microns to less than 200 microns.

In certain embodiments, at least 75% of the controlled release particles have a fracture strength of from about 0.2 MPa to about 30 MPa.

In certain embodiments, the composition is a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

In certain embodiments, the composition further comprises at least one suspension agent to suspend the controlled release particles, wherein the at least one suspension agent is at least one member selected from the group consisting of a rheology modifier, a structurant and a thickener.

In certain embodiments, the at least one suspension agent has a high shear viscosity at, 20 sec-1 shear rate and at 21° C., of from 1 to 7000 cps and a low shear viscosity, at 0.5 sec-1 shear rate at 21° C., of greater than 1000 cps.

In certain embodiments, the composition is a fluid having a high shear viscosity, at 20 sec-1 and at 21° C., of from 50 to 3000 cps and a low shear viscosity, at 0.5 sec-1 shear rate at 21° C., of greater than 1000 cps.

In certain embodiments, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition comprises at least two different controlled release technologies, which release different hydrophobic active ingredients and are selected from the group consisting of friction-triggered release microcapsules and water-triggered release microcapsules.

In certain embodiments, the at least one hydrophobic active ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

In certain embodiments, the desiccant is a member selected from the group consisting of calcium sulfate, sodium sulfate, calcium silicate, hydrophilic aluminosilicates, magnesium sulfate, alumina, silica gel, crosslinked polyacrylates and combinations thereof.

In certain embodiments, the composition has an Environmental Biodegradability greater than about 50%.

A second aspect of the invention is a method for preparing a composition of the invention, which comprises the steps of:

(a) preparing a hydrophobic oil phase comprising the at least one hydrophobic active ingredient, at least one urethane-acrylate oligomer, at least one acrylamide, at least one initiator and at least one water dispersible acrylate;

(b) heating the hydrophobic oil phase to provide a homogeneous hydrophobic solution;

(c) preparing an aqueous phase comprising water and a water soluble emulsifier;

(d) combining the homogeneous hydrophobic phase and the aqueous phase with agitation conditions to provide a mixture containing droplets of a predetermined particle size;

(e) adding to the mixture an amount of an amine, wherein a portion of the amount of the amine is optionally added to the aqueous phase before the combining step;

(f) adjusting a pH of the mixture of step (e) to at least about 8 to about 11 using an organic base;

(g) maintaining agitation of the mixture of step (f) for a period of at least about 1 hour to about 10 hours at a temperature less than 40° C.;

(h) adding an additional amount of the at least one acrylamide and an additional amount of the at least one initiator to the mixture of step (g);

(i) heating the mixture of step (h) to about 70° C. to about 99° C. for a duration of about 1 hour to about 16 hours; and (j) cooling the mixture of step (i) to room temperature to provide the composition.

In certain embodiments, the method further comprises the step of adding suspending agents to the mixture of step (j) to minimize phase separation of the controlled release particles.

In certain embodiments, the method further comprises the steps of:

adding a polysaccharide to the mixture of step (j) to provide a slurry;

dehydrating the slurry to make a powder;

adding a silica flow aid to the powder to provide a powder mixture; and heating the powder mixture within a temperature range of 130-185° C. for 20 minutes.

In certain embodiments, the powder mixture is heated by using convective, conductive, or radiative heat transfer.

BRIEF DESCRIPTION OF SEVERAL VIEWS OF THE DRAWINGS

The invention will be described in conjunction with the following drawings, wherein.

DETAILED DESCRIPTION OF PREFERRED EMBODIMENTS OF THE INVENTION

Glossary

Figure 1A:
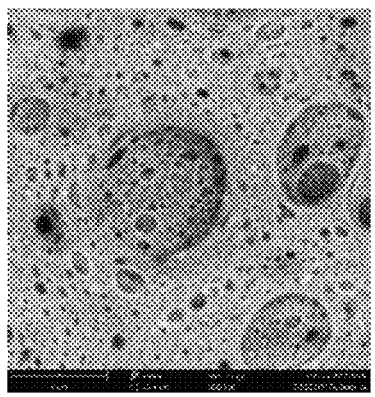
FIGS. 1A, 1B and 1C show Scanning Electron Micrographs (SEMs) of capsule shell material developed from dispersed phase, where there is independent functionality of acrylate and isocyanate.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell" and "wall" are synonyms, which refer to barriers at least partially surrounding the core of the particles of the invention.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein "cleaning and/or treatment compositions" means products comprising fluid laundry detergents, fabric enhancers, laundry and/or rinse additives, fluid dishwashing detergents, fluid hard surface cleaning and/or treatment compositions, fluid toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles.

The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks, in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin. The bar soap can also be in the form of a soft solid which is compliant to the body. The bar soap additionally can be wrapped in a substrate which remains on the bar during use.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Environmental Biodegradability testing is carried out according to protocol OECD 301D. 5 mg/L material is placed into BOD bottles in water collected from the Lehigh River (Bethlehem, Pa.). The samples consist of a negative control (a polyacrylate that is not biodegradable), a positive control (polysaccharide that is known to be fully biodegradable), test samples of unknown degradability, and when possible, a sample that simply combines the raw materials used to make the polyacrylate microcapsules, but not crosslinked. The bottles are checked for dissolved oxygen at 0, 7, 14, and 28 days. Intermittent points can also be taken since an asymptotic value may be reached much sooner than 28 days. The percent degradation is analyzed against the positive control polysaccharide.

Particles

The invention addresses one or more of the prior art deficiencies described above by providing controlled release particles. The particles are particularly well-suited for use in encapsulation of hydrophobic, nonpolar materials. The controlled release particles are preferably anhydrous and sufficiently friable to release the hydrophobic active ingredient in response to friction.

Referring to FIGS. 10A-10F, capsule (or particle) 12 comprises core 14 comprising at least one hydrophobic active ingredient and wall (or shell) 16 at least partially surrounding core 14. The wall comprises from inside to outside inner layer 18, intermediate layer 20, outer layer 22 and optional outer layer 24.

The particles are preferably used in a consumer product composition, such as, e.g., a cleaning composition, a fabric care composition and/or a personal care composition.

In one aspect, the controlled release particles suspended in an aqueous suspension comprise 18-40 wt. % of a hydrophobic active ingredient, 0.55-9.3 wt. % of an oligomer containing acrylate functionalities and isocyanate functionalities, 0.15-2.6 wt. % of an amine, 0.2-3 wt. % of an acrylamide, 0.2-3.8 wt. % initiator, 0.2-3.2 wt. % water dispersible acrylate, 1.5-8.6 wt. % emulsifier and 50-56 wt. % water, and the hydrophobic active ingredient is encapsulated in a crosslinked polymer matrix effective to retain the hydrophobic active ingredient upon exposure to water and effective to release the hydrophobic active ingredient in response to friction.

In certain embodiments, the aqueous suspension is dehydrated to yield solid particulates. The resulting dry powder controlled release particles comprise 31-62 wt. % of a hydrophobic active ingredient, 0.9-16 wt. % of an oligomer containing acrylate functionalities and isocyanate functionalities, 0.2-4.4 wt. % of an amine, 0.3-5 wt. % of an acrylamide, 10-23 wt. % of a polysaccharide, 0.35-6.5 wt. % initiator, 0.3-5.5 wt. % water dispersible acrylate, 2.5-13.5 wt. % emulsifier, 0-1.5 wt. % deposition aid, 0.5-1.0 wt. % silica, optionally 0.10-1.5 wt. % of a desiccant, wherein the hydrophobic active ingredient is encapsulated in a crosslinked polymer matrix effective to retain the hydrophobic active ingredient upon exposure to water and effective to release the hydrophobic active ingredient in response to friction.

The acrylate copolymer preferably comprises a member selected from the group consisting of a urethane acrylate oligomer bearing both acrylate and isocyanate functionalities, wherein the isocyanate content in the oligomer ranges from about 5 wt. % to about 15 wt. %, wherein the acrylate content in the oligomer can be from about 20 wt. % to about 50 wt. %. The acrylate copolymer preferably comprises Sartomer CN9302.

The copolymer of polyacrylamide and polyacrylate preferably comprises a reaction product of two or more materials comprising 1) a water-soluble monomer containing at least one vinyl group, preferably an ethylenically unsaturated carboxylic acid amide of a polyamine, and 2) a water dispersible acrylate comprising ethylenically unsaturated monomers manifesting poor to moderately hydrophilic properties, having a water solubility less than 5 grams per liter at 25° C. Suitable water-soluble vinyl monomers include, for example, N,N'-methylene-bis-acrylamide, N,N'-methylene-bis-methacrylamide, and other lower alkylidene-bis-acrylamides. Suitable water dispersible acrylates include, for example, ethylene glycol dimethacrylate, neopentyl glycol diacrylate, ethoxylated (4) bisphenol A diacrylate and pentaerythritol tetraacrylate.

The polyurea preferably comprises a reaction product of 1) an isocyanate functionality and 2) an amine functionality. Preferably, the isocyanate functionality is provided by urethane acrylate oligomers bearing both acrylate and isocyanate functionalities, or by a 50/50 blend of 4,4'-MDI (methylene diphenyl diisocyanate) and 2,4-MDI (Mondur ML). Preferably, the amine functionality is provided by, for example, acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine and Girard's reagent.

The quaternary amine is preferably a material that has a primary amine moiety and a quaternary amine moiety. The primary amine moiety can preferably react with isocyanate functionality to form a polyurea layer, and the highly polar quaternary amine functionality interacts with the surrounding aqueous phase. Suitable quaternary amine materials include, for example, Girard's reagent. Other suitable quaternary amines include but are not limited to compounds represented by formulas (1)-(4) below.

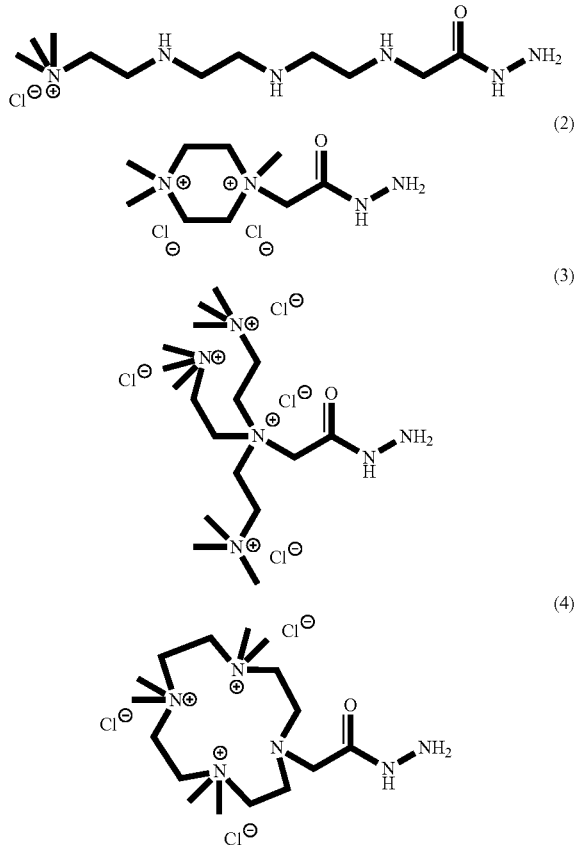

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 47 wt. % or 59 wt. % or 66 wt. % to 73 wt. % or 78 wt. % or 81 wt. % or 93.5 wt. %, wherein the weight percentages are based on the weight of hydrophobic active divided by the weight of dry matter in the composition.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an LogP (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, e.g., N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like.

Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Fungicidal compounds which in the present invention include isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone, 4,5-Dichloro-2-n-octyl-3 (2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point. Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying resin materials include unsaturated natural resins such as rosin or derivatives thereof, such as rosin esters of polyols such as glycerol or pentaerythritol, hydrogenated rosins or dehydrogenerated rosins.

Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil. Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of oil thickening agents are waxes mentioned above, modified organopolysiloxanes, silicone gums, hydrogenated castor oil, paraffin oils, polyolefins, and the like.

The emulsifier is present in the suspension, on a dry basis (weight of emulsifier per weight of dry matter in the suspension), of the invention in an amount effective to achieve the desired particle size distribution. The amount can be, e.g., from about 1.5 wt. % to about 10 wt. % or at least 1.5 wt. %, or at least 5 wt. % or at least 7.4 wt. % or at least 8.2 wt. %, or at least 10 wt. % or not greater than 10 wt. %.

Emulsifiers of all types are suitable for use in the practice of the present process though it is to be appreciated, and those skilled in the art will readily recognize that different systems, e.g., different core monomer and/or core materials, will be better suited with one or more classes of emulsifiers than others. Specifically, while the present teachings are applicable to anionic, cationic, non-ionic and amphoteric emulsifiers generally, preferred emulsifiers are the cationic and non-ionic emulsifiers, particularly those having polyalkylether units, especially polyethylene oxide units, with degrees of polymerization of the alkylene ether unit of greater than about 6. Preferred emulsifiers are those which significantly reduce the interfacial tension between the continuous water phase and dispersed oil phase composition, and thereby reduce the tendency for droplet coalescence. In this regard, generally the emulsifiers for use in the water phase for aiding in the oil in water emulsion or dispersion will have HLB values of from 11 to 17. Of course, emulsifiers/surfactants of lower and higher HLB values that achieve the same objective as noted are also included.

Exemplary emulsifiers include, but are not limited to polyvinyl alcohols; cellulose derivatives such as ethyl hydroxyethyl cellulose, 2-hydroxyethyl cellulose, hydroxybutyl methylcellulose, hydroxypropyl methylcellulose, etc.; gums such as acacia gum, gum arabic, konjac gum, and xantham gum; poly(meth)acrylic acids and derivatives; and poly(styrene-co-maleic acid) and derivatives and the like. Most preferably, the emulsifier/emulsion stabilizer is a polyvinyl pyrrolidone, copolymers of polyvinyl pyrrolidone with vinyl acetate, vinyl alcohol, vinyl imidazole; polyglycerol oleates.

Additional exemplary anionic surfactants and classes of anionic surfactants suitable for use in the practice of the present invention include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sutfoalkylamides and salts thereof such as N-methyl-N-oleoyltaurate Na salt; polyoxyalkylene alkylphenol carboxylates; polyoxyalkylene alcohol carboxylates alkyl polyglycosidelalkenyl succinic anhydride condensation products; alkyl ester sulfates; naphthalene sulfonates; naphthalene formaldehyde condensates; alkyl sulfonamides; sufonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester calcium alkylbenzene sulfonate; ethoxylated tridecylalcohol phosphate ester, dialkyl sulfosuccinates; perfluoro (C6-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglykosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilauryl sulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Exemplary amphoteric and cationic emulsifiers include alkylpolyglycosides; betaines; sulfobetaines; glycinates; alkanol amides of C8 to C18 fatty acids and C8 to C18 fatty amine polyalkoxylates; C1 to C18 alkyldimethylbenzylammonium chlorides; coconut alkyldimethylaminoacetic acids: phosphate esters of C8 to C18 fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Suitable cationic acrylates include, but are not limited to [2-(Acryloyloxy)ethyl]trimethylammonium methyl sulfate solution, 80% in water (Sigma catalog #408115), [2-(Methacryloyloxy)ethyl]trimethylammonium methyl sulfate solution, 80% in water (Sigma Cat #408123), [3-(Methacryloylamino)propyl]trimethylammonium chloride solution, 50% in water (Sigma Cat #280658), (3-Acrylamidopropyl)trimethylammonium chloride solution, 75% in water (Sigma Cat #448281), [2-(Acryloyloxy)ethyl]trimethylammonium chloride solution (Sigma Cat #496146).

Suitable non-ionic emulsifiers are characterized as having at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol;

ethoxylated castor oil; and ethoxylated nonylphenol; alkoxylated alcohols, amines or acids; amides of fatty acids such as stearamide, lauramide diethanolamide, and lauramide monoethanolamide; long chain fatty alcohols such as cetyl alcohol and stearyl alcohol; glycerol esters such as glyceryl laurate; polyoxyalkylene glycols and alkyl and aryl ethers of polyoxyalkylene glycols such as polyoxyethylene glycol nonylphenyl ether and polypropylene glycol stearyl ether. Polyethylene glycol oligomers and alkyl or aryl ethers or esters of oligomeric polyethylene glycol are preferred. Also preferred as non-ionic emulsifiers are polyvinyl alcohol, polyvinyl acetate, copolymers of polyvinyl alcohol and polyvinylacetate, carboxylated or partially hydrolyzed polyvinyl alcohol, methyl cellulose, various latex materials, stearates, lecithins, and various surfactants. It is known that polyvinyl alcohol is typically prepared by the partial or complete hydrolysis of polyvinyl acetate. Accordingly, by reference to polyvinyl alcohol we intend to include both completely and partially hydrolyzed polyvinyl acetate. With respect to the latter, it is preferred that the polyvinyl acetate be at least 50 mole % hydrolyzed, more preferably, at least 75 mole % hydrolyzed.

The amine preferably comprises a member selected from the group consisting of acidic amines such as lysine hydrochloride, urea, tryptophan hydrochloride, guanidine hydrochloride, and the like; neutral amines such as aniline, cyanamide, 4-aminobenzoic acid, and the like; and basic amines such as ethylenediamine, diethylenetriamine, guanidine, Girard's reagent, and the like. Generally, amines are listed by their pKa values, and this defines whether the amine is acidic, basic, or neutral.

The amine is present in particles of the invention in an amount effective to crosslink the isocyanate moiety on the oligomer to an extent effective to provide the particles with desired durability. The amount of amine on a dry basis (weight of amine per weight of dry matter in the suspension) can be, e.g., from 0.1 wt. % or 0.6 wt. % or 0.9 wt. % or 1.3 wt. % to 1.8 wt. % or 2.3 wt. % or 3.3 wt. %.

In certain embodiments, the acrylamide comprises a member selected from the group consisting of water soluble terpolymers. The water-soluble terpolymer of this invention consists essentially of a water-soluble monomer containing at least one vinyl groups, preferably an ethylenically unsaturated carboxylic acid amide of a polyamine. Suitable water-soluble vinyl monomers include, for example, N,N'-methylene-bis-acrylamide, N,N'-methylene-bis-methacrylamide, other lower alkylidene-bis-acrylamides where the alkylidene group has up to four carbon atoms, ethylene glycol diacrylate, ethylene glycol dimethacrylate, and propylene glycol dimethacrylate. N,N'-methylene-bis-acrylamide is most preferred. Higher amounts of polyvinyl monomer can lead to partial or complete water insolubility of the terpolymers.

The amount of acrylamide on a dry basis (weight of acrylamide per weight of dry matter in the suspension) can be, e.g., about 0.2 wt. % to about 6.8 wt. %, or at least 0.2 wt. %, or at least 1.3 wt. %, or at least 1.8 wt. %, or at least 2.6 wt. %, or at least 3.7 wt. %, or at least 4.8 wt. %, or at least 6.8 wt. %, or not more than 6.8 wt. % of the particles.

The water dispersible acrylate is preferably a member selected from the group consisting of ethylenically unsaturated monomers manifesting poor to moderately hydrophilic properties, include by way of illustration and not limitation, allyl meth acrylate, triethylene glycol dimethacrylate, ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates, tetraethylene glycol dimethacrylate, polyethylene glycol dimethacrylate, 1,3-butylene glycol diacrylate, 1,4-butanediol dimethacrylate, 1,4-butaneidiol diacrylate, diethylene glycol diacrylate, 1,6-hexanediol diacrylate, 1,6-hexanediol dimethacrylate, neo pentylglycol diacrylate, polyethylene glycol diacrylate, tetraethylene glycol diacrylate, triethylene glycol diacrylate, 1,3-butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpro panetriacrylate, pentaerythritol triacrylate, ethoxylated trim ethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate. The desired water dispersible acrylate is insufficiently hydrophilic such that it will not form a gel as it oligomerizes in the water phase and, preferably, is sufficiently hydrophobic, but not so hydrophobic, such that oligomers thereof will tend to migrate to the water/oil phase interface rather than form discrete particles or beads of the polymerized polymer in the water phase. Generally, a poor to moderately hydrophilic monomer is one that has a solubility of less than about 40 grams per liter (g/L), or even less than 30 g/L, or preferably from about 0.1 g/L to about 40 g/L, or even from about 0.1 g/L to 25 g/L, or even from about 5 g/L to 30 g/L, or even from about 10 to 25 g/L as measured in deionized water at 20° C.

The amount of water dispersible acrylate on a dry basis (weight of water dispersible acrylate per weight of dry matter in the suspension) can be, e.g., from about 0.6 wt. % to about 18.8 wt. %, or at least 0.6 wt. %, or at least 3.6 wt. % or at least 5.0 wt. % or at least 7.3 wt. % or at least 10.3 wt. % or at least 13.3 wt. %, or at least 18.8 wt. %, or no more than 18.8 wt. % of the particles.

The water phase compositions and the hydrophobic oil phase compositions may further contain other ingredients conventional in the art including, e.g., chain transfer agents and/or agents which help control the molecular weight/degree of polymerization of the wall forming monomer, thereby aiding in the movement of the oligomer through the respective oil phase and water phase compositions. Suitable chain transfer agents include, but are not limited to, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercaptoproprionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present, the chain transfer agents are preferably used in amounts ranging from 0.01 to 5%, preferably from 0.5 to 3%, by weight with respect to the monomers and/or oligomers employed.

Preferred free radical initiators include peroxy initiators, azo initiators, peroxides, and compounds such as 2,2'-azobismethylbutyronitrile and dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'- azobis (2,4-dimethylpentanenitrile), 2,2'-azobis (2,4-dimethylvale ronitrile), 2,2'-azobis(2-methylpropanenitrile), 2,2'-azobis (methylbutyronitrile), 1,1'-azobis (cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl) peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di t-amyl peroxide, 2,5-dimethyl-2, 5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably, the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps of wall formation and hardening or polymerizing of the capsule wall material. The amount of initiator (weight of initiator divided by the weight of dry matter in the suspension) can be, e.g., from about 0.13 wt. % to about 4.2 wt. %, or at least 0.13 wt. %, or at least 0.8 wt. %, or at least 2.3 wt. %, or at least 3.0 wt. %, or at least 4.2 wt. %, or no more than 4.2 wt. % of the particles.

The silica flow aid is present in the particles in an amount effective to minimize or eliminate clumping and the presence of flakes in the particles. The amount of silica flow aid on a dry basis (weight of silica per weight of dry matter in suspension) can be, e.g., from 0.05 wt. % or 0.10 wt. % or 0.5 wt. % or 1 wt. % to 2.5 wt. % or 5 wt. % or 7.5 wt. % or 10 wt. %.

The silica flow aid is preferably a precipitated silica and more preferably a fumed silica. Hydrophobic silicas are preferred. Silicas that have a surface area greater than 60 $m^2/g$ are more preferred. Preferred fumed silicas include AEROSIL R 812. Preferred precipitated silicas include SYLOID 244, which is hydrophobic and ZEOTHIX, which is hydrophilic. Alternatively, the silica flow aid comprises calcium silicate, such as Hubersorb 250 or 600 grades sold by Huber Corporation. Alternatively, the silica flow aid is an aluminosilicate such as the Zeolex grades sold by Huber Corporation.

Optionally, a desiccant is added to the powder to absorb the moisture that is released from the particle during heating, such that the moisture does not act to plasticize the particle and form large aggregates. Suitable desiccants include but are not limited to calcium sulfate, sodium sulfate, calcium silicate, hydrophilic aluminosilicates, magnesium sulfate, silica gel, crosslinked polyacrylates, and the like. It is desirable to have the desiccant particle size at least 5 times the median particle size of the powder being heated, such that after the powder heating process, the desiccants can be removed via sieving. The amount on a dry basis (weight of desiccant per weight of dry matter in the suspension) can be, e.g., from 0.05 wt. % or 0.10 wt. % or 0.5 wt. % or 1 wt. % to 2.5 wt. % or 5 wt. % or 7.5 wt. % or 10 wt. %.

Cationic particles have a higher probability of adhering to anionic fabric in the laundering environment. Amine-functionality containing materials that can be incorporated into the spray-ready emulsion, which may have a favorable effect on adhesion of particles onto skin, hair, or fabric substrates comprise a polymer selected from the group consisting of polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, copolymers of polyvinylamine and polvyinylalcohol oligimers of amines, in one aspect a diethylenetriamine, ethylene diamine, bis(3-aminopropyl)piperazine, N,N-Bis-(3-aminopropyl) methylamine, tris(2-aminoethyl)amine and mixtures thereof; polyethyleneimime, a derivatized polyethyleneimine, in one aspect an ethoxylated polyethyleneimine; diester quaternary ammonium surfactants such as methyl bis-[ethyl(coconut)]-2-hydroxyethyl ammonium methyl sulfate, methyl bis-[ethyl(decyl)]-2-hydroxyethyl ammonium methyl sulfate, methyl bis-[ethyl(dodeceyl)]-2-hydroxyethyl ammonium methyl sulfate, methyl bis-[ethyl(lauryl)]-2-hydroxyethyl ammonium methyl sulfate, methyl bis-[ethyl(palmityl)]-2-hydroxyethyl ammonium methyl sulfate, methyl bis-[ethyl(soft-tallow)]-2-hydroxyethyl ammonium methyl sulfate, and the like; diester quat combined with laminate nanoclays such as laponite, bentonite, montmorillonite, and the like; chitosan with various degrees of deacetylation, carboxymethyl chitosans, glycol chitosans, whey protein, sodium caseinate, silk protein, whey protein, polyamines, polysaccharides with cationic modification, and mixtures thereof. Polysaccharides can be employed with cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Furthermore, up to 5 different types of functional groups may be attached to the polysaccharides. Also, polymer graft chains may be differently modified than the backbone. The counterions can be any halide ion or organic counter ion. The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc. The preferred cationic guar has a molecular weight of from about 50,000 to about 5,000,000. The preferred cationic guar products are Jaguar C-162 and Jaguar C-17 and are commercially available from Rhodia Inc.

The deposition aid is present in the controlled release particles in an amount on a dry basis (weight of deposition aid per weight of dry matter in the suspension) from 0.5 wt. % or 1 wt. % or 1.5 wt. % or 3.5 wt. % to 5 wt. % or 7 wt. % of the weight of the particle.

The controlled release particles are preferably spherical but non-spherical shapes are also within the scope of the invention. The particles preferably have a diameter from 0.05-250 microns, or from 0.1 microns to less than 100 microns.

Method of Making the Particles

The controlled release particles according to the present teaching are made in a multi-step process as described below. For convenience, the process is presented in the preferred mode which involves one aqueous phase composition and one hydrophobic oil phase composition. Nonetheless, those skilled in the art will readily appreciate that the aqueous phase composition may be prepared as a dual phase composition to which the hydrophobic oil phase composition is added or a three or more components composition where various ingredients are preferably isolated from one another until desired so as to avoid undue or undesired activation of the aqueous phase monomers or oligomers.

The hydrophobic oil phase composition is formed by combining the hydrophobic active core material with oil soluble monomers and oligomers. Most preferably this is conducted under moderate increased temperature so as to facilitate the solubilization or suspension of the monomers, oligomers, and other ingredients that may be present, including nucleating agents, in the core material. This is particularly useful if the core material is a solid or wax or a high viscosity material. Once a stable solution or suspension of the core material is prepared, the hydrophobic oil phase initiator is then added to the combination and the composition mixed to ensure good dispersion of the hydrophobic oil phase initiator. Once again, if the temperature of the mixture had been elevated to aid in getting the hydrophobic oil phase monomer into solution/suspension, then the mixture should be cooled or allowed to cool to a temperature that is safely below the lowest key activation temperature of the one or more hydrophobic oil phase initiators. It is best to cool the resultant oil phase composition before adding it to the aqueous phase composition.

The mixture is agitated until the desired droplet size of oil phase composition is attained. In order to establish a wall at the oil-water interface, an amine is added to the aqueous phase followed by pH adjustment. The addition of the amine partitions the dual-functional acrylate oligomer (i.e., the acylate copolymer) in the hydrophobic oil phase to the interface. The interfacial reaction of the amine with the isocyanate functionality results in a membrane at the oil-water interface that stabilizes the oil droplets. Droplets are preferably from about 10 microns to about 75 microns, and more preferably from about 20 microns to about 50 microns in volume average diameter. Once this membrane is established, no further decrease in particle size of the oil droplets is observed. However, this membrane is porous. The reactor contents are agitated for 30 minutes to 5 hours, depending on the emulsifying properties of the hydrophobic oil phase. It is desired to maintain a temperature of the reactor below 40° C., in order to facilitate controlled membrane formation.

At this point, isolation of the microcapsule shows a developed membrane at the interface; however, the membrane has larger pores. A mixture of acrylamide material and initiator in water is added to the reactor vessel. As water-soluble monomers one can use more especially acrylamide and N,N'-methylene-bis-acrylamide, or oil-soluble monomers such as, preferably, acrylic acid and acrylic acid methyl ester. In this step of the process one can also proceed in such a way that water and monomers are stirred alone into the hydrophobic active, emulsifier containing liquid, or lipophilic solvent and lipophilic monomers are inserted in the hydrophilic, emulsifier containing liquid, thereupon the concentrated, and where appropriate colloidal, aqueous or oily solution of the active enclosure material is added to the solution obtained.

Optionally, a mixture of water dispersible acrylate in water and initiator is also added to the reactor vessel. The temperature of the reaction vessel is raised to the activation temperature of the hydrophobic oil phase initiator and aqueous phase initiator. It is desired to use the same initiator in both phases, or alternatively, initiators that have activation temperatures that are within 5° C. of each other. If multiple initiators are incorporated into the hydrophobic oil phase and/or aqueous phase, it is desired to raise the temperature to the activation temperature of the low temperature initiator. Since the dual functional acrylate oligomer is already at the oil-water interface, the increase in temperature activates the crosslinking of acrylate moieties to increase the crosslink density of the shell to form a strong polymer composition. Acrylamides and water dispersible acrylates from the aqueous phase will also partition to the interface to increase the crosslink density of the shell. Here, the higher temperature is maintained until the capsules are fully formed, generally from about 1 to 8 hours.

Although not critical to the basic embodiment of the present teaching, the rate of temperature increase in the activation of the initiators can also influence the ultimate performance and characteristics of the resultant microcapsules. In this regard it is preferred that temperature increases be performed over an extended period of time, preferably over a period of 25 to 40 minutes, more preferably about 30 minutes. The rate of increase during that period may vary from about 20° C. per hour to about 40° C. per hour. Of course, these are general ranges and the same may be somewhat lower or somewhat higher depending upon the selected materials and the activation temperatures of the initiators.

In certain embodiments, the suspension of controlled release particles is dehydrated in order to expose the particles to a higher temperature to achieve a higher degree of crosslinking of the monomers.

In certain embodiments of providing a powder composition of the invention, spray drying of the particle suspension is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

In powder composition embodiments, the silica flow aid is added to the dry powder to improve the flowability of the powder. Addition of the silica flow aid minimizes the agglomeration of particles during the heating, packing, and conveyance processes.

In powder composition embodiments, it is preferred to heat the powder mixture within a temperature range of 110-150° C. for a period of 10 to 30 minutes achieve the desired interaction between oligomer, initiator, amine, and acrylamide, and acrylates to provide a controlled release particle that can provide friction-triggered release of the encapsulated active.

Curing conditions can be adjusted to achieve a desired leakage stability and release profile of the encapsulated active.

Curing of the particles can be achieved by any suitable heating means. There are three primary methods of heat transfer: convective, conductive, and radiative. Convective heat transfer uses air to fluidize the particles, and the temperature of the air is manipulated to achieve the desired heating. Conductive heat transfer utilizes either electric heating in a kiln, or oil heating in a jacketed paddle mixer (auger mixer, cement mixer, ribbon blender, U-trough mixer, and the like). The powder is rotated in the mixer and heating occurs by transfer of heat from the metal surface of the mixer to the powder touching that surface. Radiative heat transfer utilizes infrared waves, radio frequency waves, microwaves to achieve the desired heating. Any of these methods can be used to achieve the desired heat treatment of the particle. Suitable heating means include but are not limited to one or more of the following: oven, rotary infrared dryers, microwave radiative dryers, radio frequency radiative dryers, kiln or calciner, steam tube dryers, tray dryers, fluid bed dryers, granulators, baking ovens, serpentine ovens, jacketed auger mixers, jacketed ribbon blenders, and the like.

Gentle agitation is preferably provided during curing to minimize fracture of the particles.

Advantages of at least some embodiments of the inventive method include at least one or at least two or at least three or at least four or all five of the following:

a) One-pot process: low porosity membrane developed from oil and aqueous phases in a single process.

b) Flexibility in active: membrane is developed at the oil-water interface via the use of interfacial polymerization. No diluents need to be added to the oil phase in order to achieve an interfacial membrane.

c) Shell thickness can be controlled by adjusting the quantity of acrylamides and co-acrylates.

d) Can be used in a variety of applications, including but not limited to household care, personal care, beauty care, etc.

e) Preferably utilizes a commercially available, relatively inexpensive spray drying technique to further engineer the particle.

Compositions Containing the Particles

The invention further comprises compositions comprising the controlled release particles. Such compositions include but are not limited baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrances (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee. Moreover, such products include, but are not limited to, a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, fluid hard surface cleaner, solid hard surface cleaner, a fluid fabric refresher spray, a diaper, an air freshening product, a nutraceutical supplement, a controlled release fertilizer, a controlled release insecticide, a controlled release dye, and a unit dose detergent comprising a detergent and the controlled release particles in a water soluble film.

Fluid compositions of the invention preferably further comprise at least one suspension agent to suspend the controlled release particles, wherein the at least one suspension agent is at least one member selected from the group consisting of a rheology modifier, a structurant and a thickener. The at least one suspension agent preferably has a high shear viscosity at, 20 $sec^{-1}$ shear rate and at 21° C., of from 1 to 7000 cps and a low shear viscosity, at 0.5 $sec^{-1}$ shear rate and at 21° C., of greater than 1000 cps or 1000-200,000 cps. In certain embodiments, the composition has a high shear viscosity, at 20 $sec^{-1}$ and at 21° C., of from 50 to 3000 cps and a low shear viscosity, at 0.5 $sec^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

The invention further encompasses a slurry comprising particles of the invention. Said slurry may be combined with an adjunct ingredient to form a composition, for example, a consumer product. In certain embodiments, the slurry comprises at least one processing aid selected from the group consisting of water, aggregate inhibiting materials such as divalent salts, particle suspending polymers, and mixtures thereof. Examples of aggregate inhibiting materials include salts that can have a charge shielding effect around the particle, such as, e.g., magnesium chloride, calcium chloride, magnesium bromide, magnesium sulfate and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In certain embodiments, the slurry comprises at least one carrier selected from the group consisting of polar solvents, including but not limited to, water, ethylene glycol, propylene glycol, polyethylene glycol, glycerol; non polar solvents, including but not limited to, mineral oil, perfume raw materials, silicone oils, hydrocarbon paraffin oils, and mixtures thereof.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition spanning a range of polarity (octanol/water partition coefficient), and boiling point.

| CAS | Name | Octanol/water Partition Coefficient (logP) | Boiling Point, °C. | wt. % |
|---|---|---|---|---|
| 67634-00-8 | Allyl_amyl_glycolate | 2.81 | 231 | 6.10% |
| 7493-57-4 | (−)-Citronellol | 2.76 | 279 | 5.11% |
| 150-84-5 | Citronellyl_acetate | 3.7 | 222 | 6.49% |
| 103-95-7 | Cyclamen_aldehyde (cymal) | 3.62 | 290 | 6.23% |
| 18592-13-7 | Dihydromyrcenol | 3.08 | 195 | 5.11% |
| 68647-72-3 | d-Limonene | 4.38 | 176 | 4.46% |
| 7452-79-1 | Ethyl_2-methylbutyrate | 1.91 | 133 | 4.26% |
| 125109-85-5 | Florhydral | 3.59 | 295 | 6.23% |
| 142-92-7 | Hexyl_acetate | 2.64 | 165 | 4.72% |
| 14901-07-6 | beta-Ionone | 4.02 | 267 | 6.29% |
| 97-54-1 | Isoeugenol | 1.85 | 264 | 5.37% |
| 2437-25-4 | Lauronitrile | 4.84 | 251 | 5.93% |
| 78-70-6 | Linalool | 2.44 | 204 | 5.05% |
| 6008-27-1 | Nonalactone | 1.3 | 201 | 5.11% |
| 88-41-5 | o-tert-Butylcyclohexyl_acetate (verdox) | 3.87 | 223 | 6.49% |
| 177772-08-6 | Undecavertol | 3.06 | 242 | 5.57% |
| 87731-18-8 | Violiff | 2.11 | 214 | 6.03% |

Thermal Gravimetric Analysis

A Thermal Gravimetric Analysis pan is exposed to a Bunsen burner to remove any residue from the pan. Approximately 5 milligrams of sample is weighed onto a pan of a Thermal Gravimetric Analyzer (Model TGA Q500). Next the sample is exposed to a temperature ramp that comprises from an initial temperature of 25° C., a heating ramp of 10° C. per minute, to a final temperature of 600° C. A graph of sample mass loss versus temperature is plotted to gain insights into transitions—water evaporation, volatile active evaporation, degradation of the microcapsule materials.

Differential Scanning Calorimetry

Approximately 5 milligrams of sample is weighed onto a pan of a Differential Scanning Calorimeter (Model DSC Q2000) and hermetically sealed. The sample pan is then exposed to a temperature ramp that comprises from an initial temperature of 25° C., a heating ramp of 10 Celsius degrees per minute, to a final temperature of 250° C., and then a temperature decrease ramp of negative 10° C. per minute, to a final temperature of 25° C. A graph of heat flow versus temperature provides insights into thermal transitions that occur in the powder.

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Detergent/Water Dissolution+Fabric Preparation

To 9.75 grams of a detergent solution (1 gram of powder detergent added to 99 grams of water, then filtered through Whatman 597 filter catalog number 10311808) is added powder or slurry that achieves a concentration of approximately 1 wt. % perfume oil in the detergent solution. For water solubility, the powder is simply dosed into water rather than detergent solution. The solution is mixed at 200 rpm with a stir bar, for 1 hour at 20° C. to simulate a cold water laundry cycle, or 33.3° C. to simulate a warm water laundry cycle. For detergent dissolution, the sample is mixed at 200 RPM for 30 minutes at 33.3° C. A pre-weighed 3 inch diameter circle of black 100% cotton fabric is placed in a Buchner funnel attached to a vacuum line. 2 mL of the solution is then poured through the fabric, followed by a wash of 2 mL water. The fabric is allowed to air dry overnight.

Odor Evaluation

There are two techniques utilized to evaluate odor of fabrics:

1) The dried fabrics from the Detergent/Water Dissolution+Fabric Preparation test is evaluated olfactively by a panel before and after rubbing.

The dried fabrics from the Detergent/Water Dissolution+Fabric Preparation test is evaluated by an Odor Meter (Shinyei Technology model OMX-SRM) before and after rubbing.

Biodegradability

Biodegradability testing is carried out according to protocol OECD 301D. 5 mg/L material is placed into Biochemical Oxygen Demand (BOD) bottles in water collected from the Lehigh River (Bethlehem, Pa.). The bottles are checked for dissolved oxygen at 0, 7, 14, and 28 days. Intermittent points can also be taken since an asymptotic value may be reached much sooner than 28 days. The percent degradation is analyzed against the positive control starch. See Example 24 for a detailed description of the analysis and calculations of Biodegradability Index.

Example 1

Capsule Shell Material Developed From Dispersed Phase—Independent Functionality

Prepare Oil Phase: 10 g of Perfume oil and 10 g of Butyl acrylate are stirred at room temperature for 15 minutes at 600-800 RPM using Caframo BDC6015, using a 4-blade pitched agitator shaft 1" diameter. Then 0.8 g of Vazo-67 is added and allowed to mix. Then, the temperature of the mixture is raised to 67° C.

Prepare Aqueous phase: 100 grams of a 5 wt. % aqueous solution of Sokalan K90P is prepared.

Emulsion Formation: The prepared oil phase is quickly added to the prepared aqueous phase, while agitating at 700-900 RPM (Caframo BDC6015, 4-blade pitched agitator shaft 1" diameter). The emulsion is stirred for 25 minutes. An aliquot is analyzed by optical microscopy to understand particle size of the emulsion. The solution is then heated to 70° C. for 5 hours.

Figure 1B:
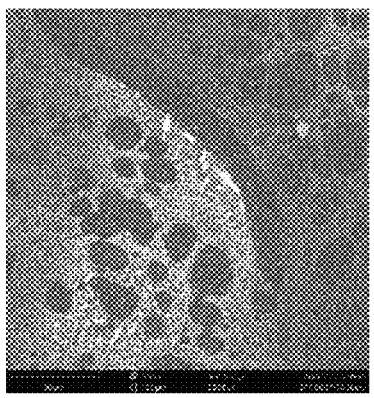
Figure 1C:
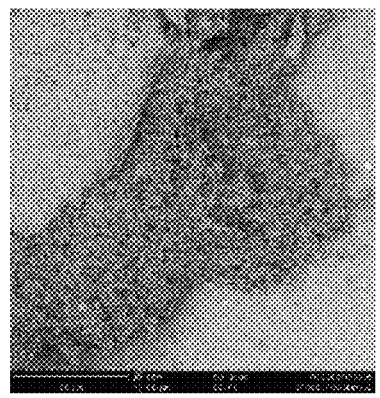

Observation: Pale yellowish color slurry is observed. After overnight stirring the emulsion has solid globules and emulsion appears to be too thick. No microcapsules are observed in FIGS. 1A, 1B and 1C.

Example 2

Acrylate+Isocyanate Functionality Capsules (No Dual Functional Acrylate Oligomer)

Materials: Perfume oil (Beige sage, 10 g), Butyl acrylate (BAc) (9.2 g), Isophorone diisocyanate (0.8 g) Vazo-67 (1.4 g) and Urea (1 g).

Prepare Oil Phase: 10 grams of Perfume oil+9.2 g of Butyl acrylate+0.8 g Isophorone Diisocyanate are stirred at room temperature for 15 minutes at 600-800 RPM using Caframo BDC6015, using a 4-blade pitched agitator shaft 1" diameter. Then 0.8 g of Vazo-67 is added and allowed to mix. Then, the temperature of the mixture is raised to 67° C.

Prepare Aqueous phase: 100 grams of a 5 wt. % aqueous solution of Sokalan K90P is prepared.

Prepare Emulsion: The prepared oil phase is quickly added to the prepared aqueous phase, while agitating at 700-900 RPM (Caframo BDC6015, 4-blade pitched agitator shaft 1" diameter). The emulsion is stirred for 25 minutes. 1.0 g of Urea (pre-dissolved in 5 g water) is then added to the mixture. After 5 minutes, adjust pH to 11 using N,N,N',N'',N'-Pentamethyldiethylenetriamine, and the mixture is stirred for 5 hours at room temperature. 0.7 g ov Vazo-67 is then added to the solution, and the contents are heated to 70 C, and maintained at 70 C for 5 hours, followed by overnight stirring while cooling of the batch.

Figure 2A:
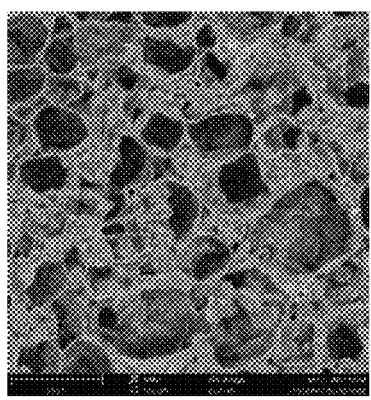
FIGS. 2A, 2B and 2C show SEMs of capsules made with acrylate and isocyanate functionality, with no dual functional acrylate oligomer.
Figure 2B:
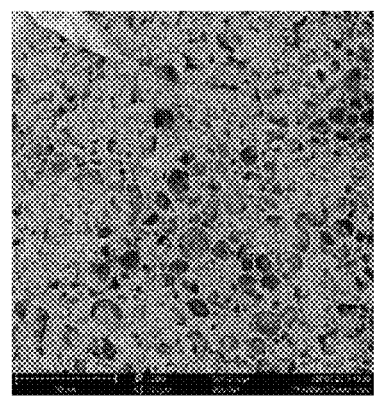
Figure 2C:
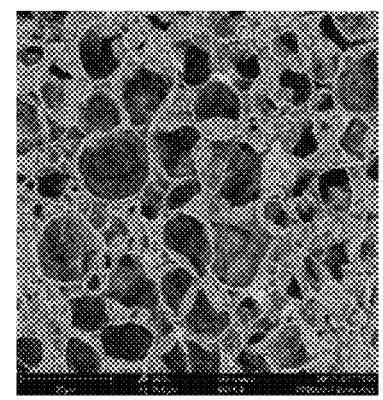

Observations: Final color of the sample appears to be in pale cream. Sample under optical microscope shows very small microcapsules if any. Sample separation by means of centrifuge led to perfume oil separation from the capsules, similar to the behavior of Example 1. Scanning Electron Microscopy in FIGS. 2A, 2B and 2C show an open, porous framework, no microcapsules.

Example 3

Acrylate+Isocyanate+Acrylamide Capsules (No Dual Functional Acrylate Oligomer)

The procedure of Example 2 is followed, with the following modifications.

After addition of urea, and reaction for 5 hours at room temperature, 1.85 g of N,N-methylenebisacrylamide in 10 mL water is added to the mixture, along with 0.7 g Vazo-67. The mixture is then heated as explained in Example 2.

Figure 3A:
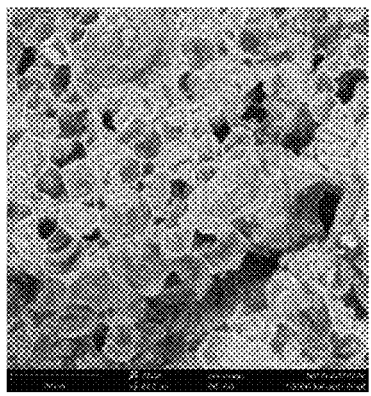
FIGS. 3A, 3B and 3C show SEMs of capsules made with acrylate, isocyanate, and acrylamide functionalities but no dual functional oligomer.
Figure 3B:
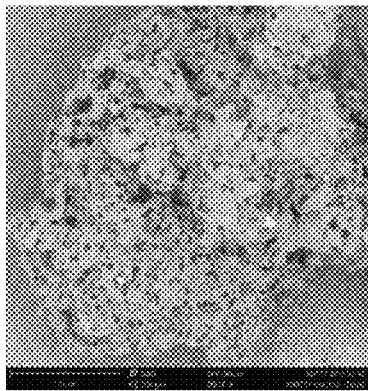
Figure 3C:
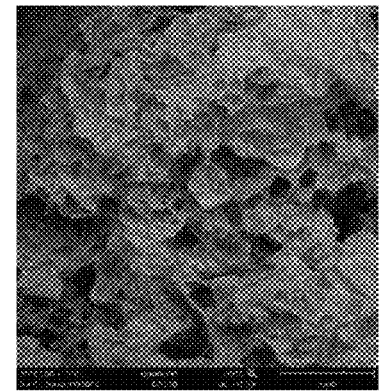

Observation: Sample analysis of optical microscope suggests cracked/deformed capsules. It is evident from Example 2 that a combination of acrylate functionality combined with isocyanate functionality does not result in capsule formation. However, addition of acrylamide may help in capsule formation, as evidenced by Scanning Electron Microscopy imaging in FIGS. 3A, 3B and 3C; however these capsules are porous.

It is our belief that in such a "dual shell" approach, the two membranes that are developed from each phase are not miscible, and generally not compatible, with one another. Because these two shell materials are not miscible in one another, sealing the pores in the developed shell is difficult. Hence, a thicker membrane is developed, but the permeability of the membrane remains high.

Example 4

Bis-Acrylamide Capsules (No Dual Functional Acrylate Oligomer)

The procedure of Example 1 is followed to make microcapsules with the exception that 10 g of Butyl Acrylate is replaced with 1.85 g N,N-methylenebisacrylamide.

Perfume oil is observed to float on top of the slurry. Optical microscopy did not show any capsule formation. This trial is a direct evidence that acrylamide by itself is not sufficient to make capsules.

Example 5

Shell Material Developed from Oil Phase, Dual Functionality Oligomer

Prepare Oil Phase: 10 g of Sartomer CN9302 is added to 10 g of perfume oil. 0.7 grams of Vazo-67 is added, and the mixture is heated to 67 C.

Prepare Aqueous phase: 100 grams of a 5 wt. % aqueous solution of Sokalan K90P is prepared.

Prepare Capsules: The prepared oil phase is quickly added to the prepared aqueous phase, while agitating at 700-900 RPM (Caframo BDC6015, 4-blade pitched agitator shaft 1" diameter). The emulsion is stirred for 25 minutes. 1.0 g of Urea (pre-dissolved in 5 g water) is then added to the mixture. After 5 minutes, adjust pH to 11 using N,N,N',N'',N'-Pentamethyldiethylenetriamine. The mixture is then stirred for 5 hours at room temperature. Then, 0.7 g of Vazo-67 is added to the solution, and the contents are heated to 70° C., and maintained at 70° C. for 5 hours, followed by overnight stirring while cooling of the batch. After 20 minutes, the product was examined for emulsion formation.

Figure 4A:
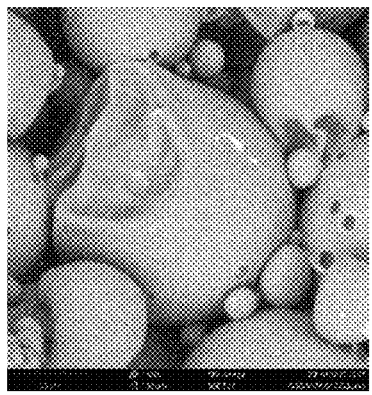
FIGS. 4A, 4B and 4C show SEMs of capsules made with shell material developed from oil phase, using dual functionality oligomer.
Figure 4B:
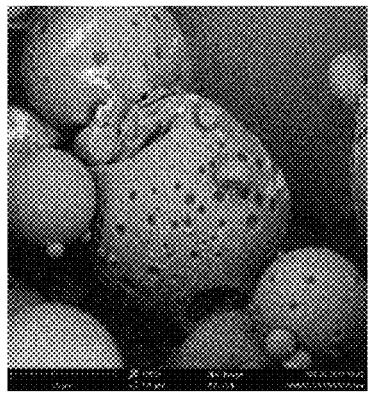
Figure 4C:
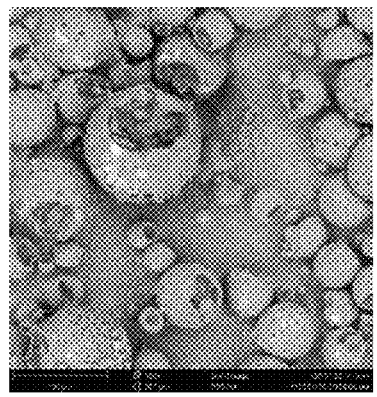

Observation: Final color of the sample is darker beige color. Under optical microscope we can see perforated, spherical capsules. There are orifices which gives us a glimpse of interiors of this capsule, shown in FIGS. 4A, 4B and 4C. The capsules are porous microspheres.

Example 6

Sealed Pores

The procedure of Example 5 is followed to make capsules, with the following modification: after the pH adjustment of the mixture, and 5 hours of reaction at room temperature, 1.85 grams of N,N-methylenebisacrylamide dispersed in 15 mL water is added to the mixture.

Figure 5A:
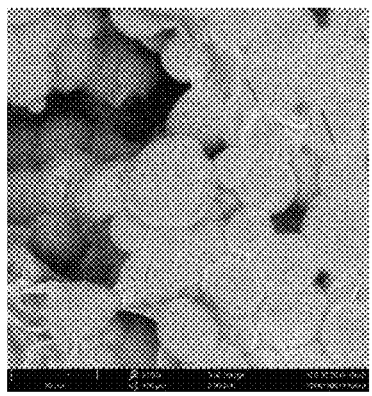
FIGS. 5A, 5B and 5C show SEMs of capsules made with dual functional oligomer and acrylamide.
Figure 5B:
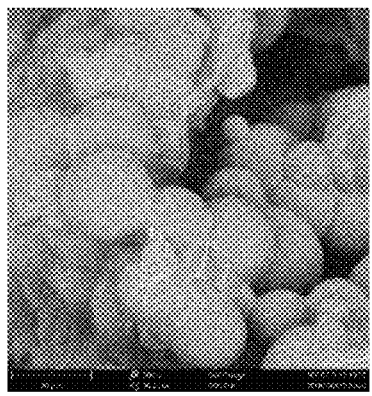
Figure 5C:
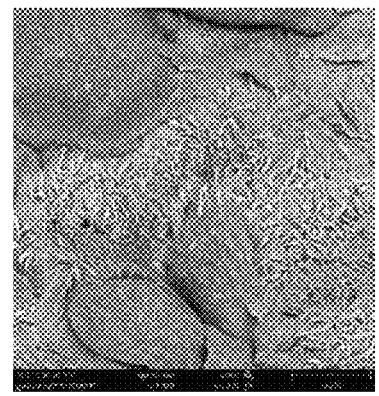

Sample under optical microscope indicates spherical capsules with a small deformation on the capsule surface. A comparison of Scanning Electron Microscopy pictures of Example 5 (FIGS. 4A, 4B and 4C) and Example 6 (FIGS. 5A, 5B and 5C) show sealing of the perforated pores.

While not being limited by theory, a comparison of Example 1 and Example 6 shows that N,N-methylenebisacrylamide is a co-reactant with the acrylate functionality of CN9302, and acts as a crosslinking agent to seal the pores when added in the aqueous phase.

Example 7

Dual Shell Capsules Using Additional Isocyanate

The procedure of Example 6 is followed to prepare microcapsules with the following modification: after addition of urea, pH adjustment, and reaction for 5 hours at room temperature, 2 grams of isophorone diisocyanate (2 g) is added to the mixture. Next, 20 grams of 10 wt. % urea aqueous solution is added, followed by pH adjustment to 11. The mixture is stirred for an additional 5 hr at room temperature. After the stipulated time, add dropwise aqueous solution of N,N-methylenebisacrylamide (3.7 g in 15 ml water) followed by fresh portion of vazo-67 (0.8 g). The mixture is stirred at 70° C. for 5 hr and the contents are allowed to cool to room temperature overnight.

Figure 6:
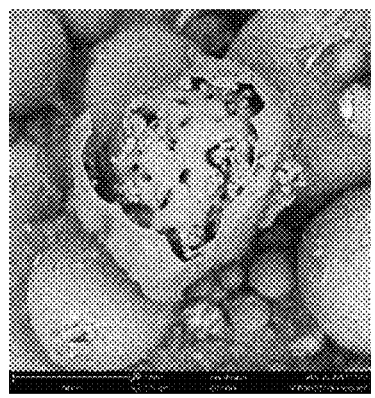
FIG. 6 shows SEMs of dual shell capsules.
Figure 7A:
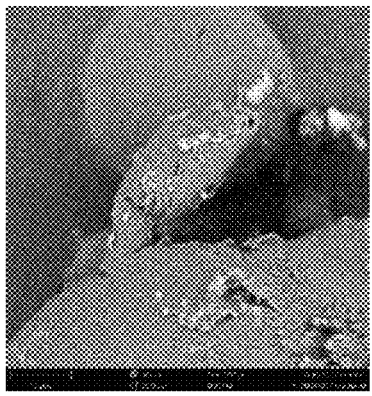
FIGS. 7A, 7B and 7C show SEMs with 37% loading.
Figure 7B:
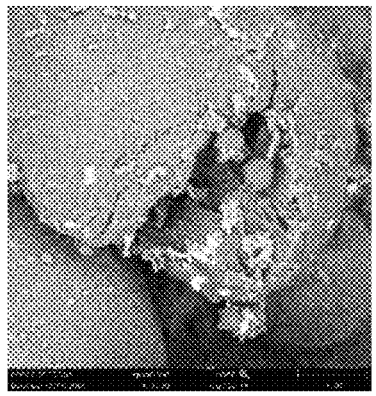
Figure 7C:
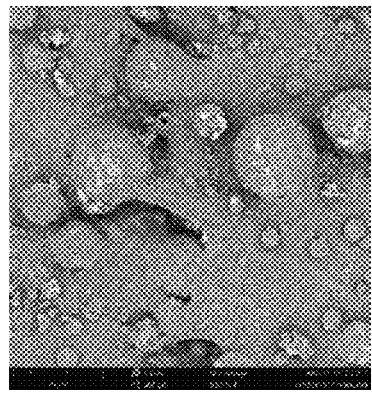
Figure 8A:
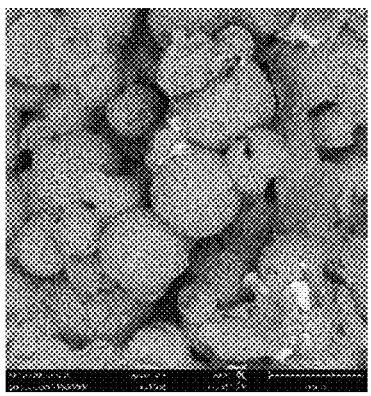
FIGS. 8A, 8B and 8C show SEMs with 60% loading.
Figure 8B:
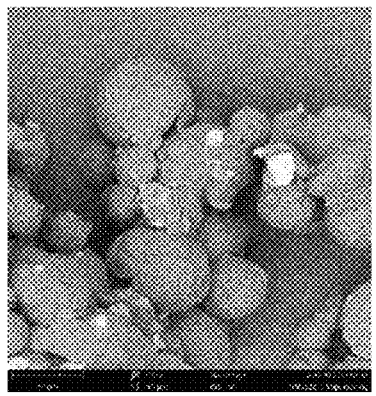
Figure 8C:
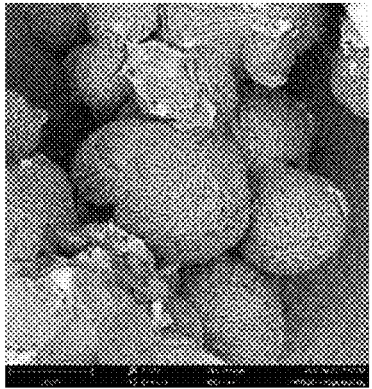
Figure 9A:
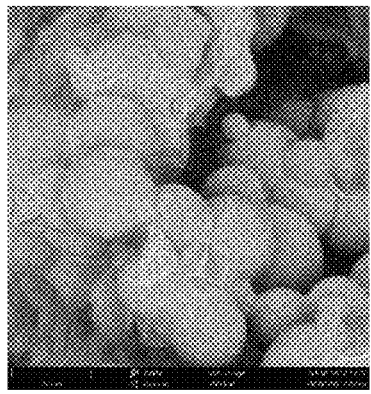
FIGS. 9A and 9B show SEMs with 80% loading.
Figure 9B:
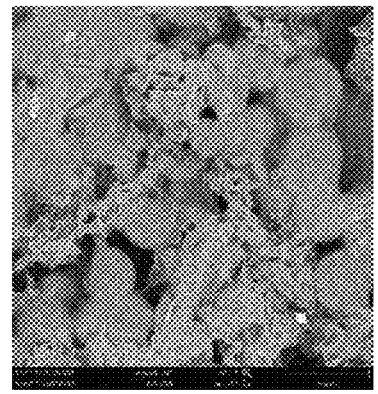
Figure 10A:
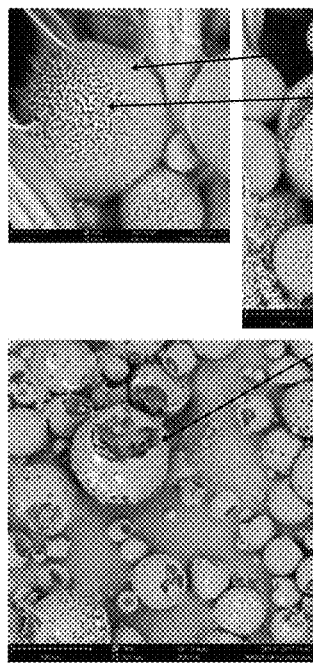
FIG. 10F shows a schematic depiction of an embodiment of a capsule of the invention with features thereof being identified in several SEMs of capsules of the invention shown in FIGS. 10A, 10B, 10C, 10D and 10E.
Figure 10B:
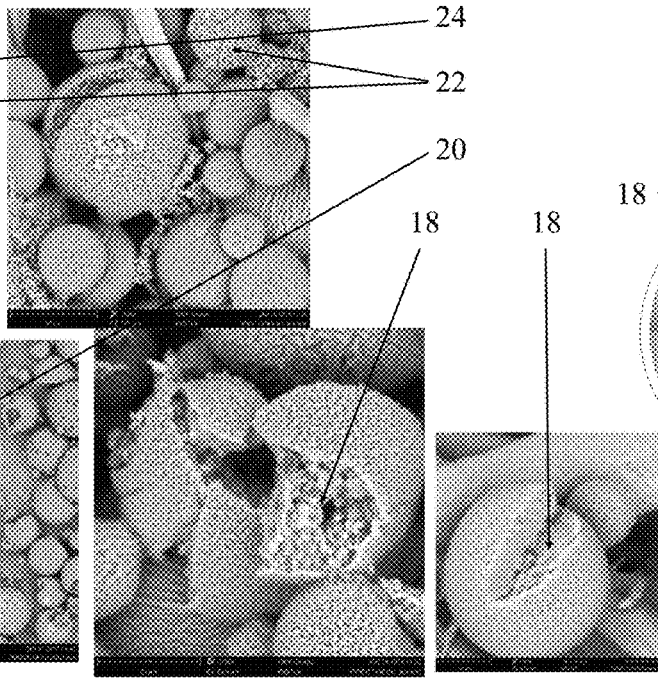
Figure 10C:
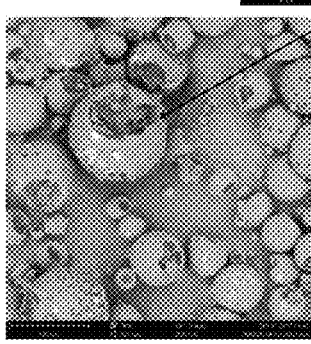
Figure 10D:
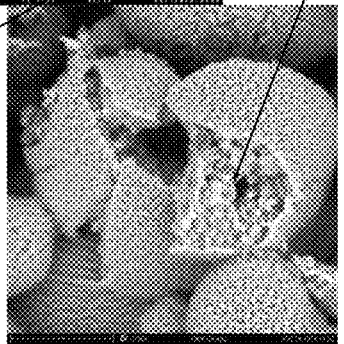
Figure 10E:
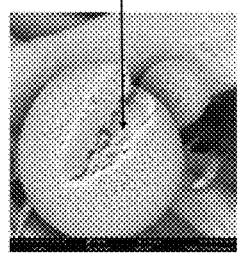
Figure 10F:
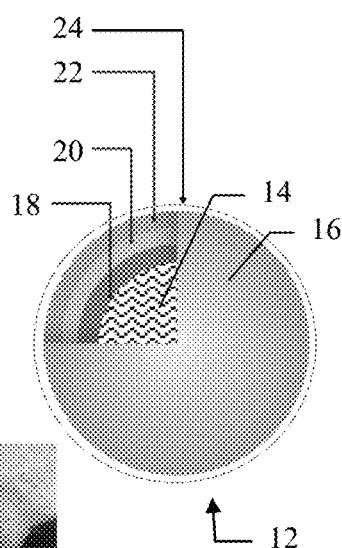

This experiment was an attempt to produce capsules with softer outer cores. From the SEM image of FIG. 6 it was very evident that isophorone diisocyanate did react with urea to form secondary or outer wall.

Example 8

Amine Type Study

The following general procedure is used to prepare capsules.

Prepare Oil Phase: 23 grams of Perfume oil, 5 g of CN9302, 0.6 g of Vazo-67, 0.93 g of N,N-methylenebisacrylamide are mixed together and stirred at room temperature for 15 minutes at 600-800 RPM using Caframo BDC6015, using a 4-blade pitched agitator shaft 1" diameter. Then, the temperature of the mixture is raised to 67° C.

Prepare Aqueous phase: 100 grams of a 5 wt. % aqueous solution of Sokalan K90P is prepared.

Prepare Emulsion: The prepared oil phase is quickly added to the prepared aqueous phase, while agitating at 700-900 RPM (Caframo BDC6015, 4-blade pitched agitator shaft 1" diameter). The emulsion is stirred for 25 minutes.

Amine addition: 0.8 g of Aniline is then added to the mixture. After 5 minutes, the pH is adjusted to 11 using N,N,N',N",N'-Pentamethyldiethylenetriamine.

Prepare Capsules: The mixture is stirred for 5 hours at room temperature. Then, 0.92 g of N,N-methylenebisacrylamide (in 15 mL water) is added to the mixture. Next, 0.6 g of Vazo-67 is then added to the solution, and the contents are heated to 70° C., and maintained at 70 C for 5 hours, followed by overnight stirring while cooling of the batch.

These capsules are Example 8A. The general procedure above is used to prepare capsules, with the following modifications during the amine addition step listed above:

Example 8B: 0.8 g of powder Melamine is then added to the mixture. After 5 minutes, the pH is adjusted to 11 using N,N,N',N",N'-Pentamethyldiethylenetriamine Example 8C: 0.8 g of powder Chitosan is then added to the mixture. After 5 minutes, the pH is adjusted to 11 using N,N,N',N",N'-Pentamethyldiethylenetriamine Example 8D: 0.8 g of urea (pre-dissolved in 5 mL water) is then added to the mixture. After 5 minutes, the pH is adjusted to 11 using N,N,N',N",N'-Pentamethyldiethylenetriamine.

Examples 8A, 8B, 8C, and 8D formed capsules.

Example 9

Acrylamide Type Study

The following general procedure is used to prepare capsules.

Prepare Oil Phase: 23 grams of Perfume oil, 5 g of CN9302, 0.6 g of Vazo-67, 0.93 g of an acrylamide are mixed together and stirred at room temperature for 15 minutes at 600-800 RPM using Caframo BDC6015, using a 4-blade pitched agitator shaft 1" diameter. Then, the temperature of the mixture is raised to 67° C.

Prepare Aqueous phase: 100 grams of a 5 wt. % aqueous solution of Sokalan K90P is prepared.

Prepare Emulsion: The prepared oil phase is quickly added to the prepared aqueous phase, while agitating at 700-900 RPM (Caframo BDC6015, 4-blade pitched agitator shaft 1" diameter). The emulsion is stirred for 25 minutes.

Amine addition: 0.8 g of Amine is then added to the mixture. After 5 minutes, the pH is adjusted to 11 using N,N,N',N",N'-Pentamethyldiethylenetriamine.

Prepare Capsules: The mixture is stirred for 5 hours at room temperature. Then, 0.92 g of an acrylamide (in 15 mL water) is added to the mixture. Next, 0.6 g of Vazo-67 is then added to the solution, and the contents are heated to 70° C., and maintained at 70° C. for 5 hours, followed by overnight stirring while cooling of the batch.

Example 9A is manufactured using N,N-methylenebisacrylamide as the acrylamide.

Example 9B is manufactured using diacetone acrylamide as the acrylamide.

Example 9C is manufactured using acylamide.

Example 9D is manufactured using 2-(Acrylolyloxy)ethyltrimthylammonium chloride.

Example 9E is manufactured using [3-acrylamidopropyl) trimethyl ammonium chloride solution.

N,N'-Methylene bisacrylamide—a diacrylamide appears to seal the pore and makes the surface of CN9302 based capsules more sturdy. On the other hand, mono acrylates such as: a) Diacetone acrylamide, b) Butyl acrylate, c) (3-Acrylamidopropyl)trimethylammonium chloride solution, d) [2-(Acryloyloxy)ethyl]trimethylammonium chloride solution do not show significant differences versus CN9302 capsules control. Finding suitable materials that develop a membrane from both oil and water phases, wherein the membrane is developed due to reaction of monomers at the interface, wherein the membrane thickness can be increased due to compatibility of the two membranes at the interface, results in microcapsules with reduced permeability.

Example 10

Perfume Loading Study

The following table summarizes additional examples of microcapsules prepared using a variety of ingredients including perfume oil.

|  | Example | | | |
| --- | --- | --- | --- | --- |
|  | 10A (grams) 37% loading | 10B (grams) 60% loading | 10C (grams) 70% loading | 10D (grams) 80% loading |
| Perfume Oil | 10 | 13 | 23 | 35 |
| CN9302 | 10 | 5 | 5 | 5 |
| Urea | 1.0 | 0.5 | 0.5 | 0.5 |
| Vazo-67 | 1.4 | 1.4 | 1.4 | 1.4 |
| Sokalan K90P 5% solution | 100 | 100 | 100 | 100 |
| Butyl acrylate | 3.7 | N/A | N/A | N/A |
| N,N-methylene-bisacrylamide | N/A | 1.85 | 1.85 | 1.85 |
| Organic Base | 0.2 | 0.2 | 0.2 | 0.2 |

Thick wall, hard to break capsules were observed mainly at 37% stage which become brittle at 80% loading. Increasing the perfume contents makes the wall of capsules leakier in nature. Detergent Dissolution Test clearly shows that optimum level of perfume loading occurs at 60%.

| Detergent Dissolution Test Table | | |
| --- | --- | --- |
| Capsule Loading (% perfume) | Detergent Dissolution Test Fabric Odor (no rub) | Detergent Dissolution Test Fabric Odor (with rub) |
| 37% | 3 | 2 |
| 60% | 2.33 | 2.33 |
| 70% | 1 | 0.33 |
| 80% | 1.65 | 1.5 |

SEM images (FIGS. 7A, 7B, 7C, 8A, 8B, 8C, 9A and 9B) show sturdy capsules, hard to break even when applied external force at 37% loading which transforms to few broken capsules with increasing loading specifically at 80%.

Example 11

Capsule Curing Study [60% Loading, Spray Drying, Curing with and without the Bisacrylamide]

The capsule slurry of Example 6 was spray dried using a co-current Bowen spray dryer, 3 ft diameter, with an inlet air temperature of 385° F. (196° C.), an outlet air temperature of 185° F. (85° C.), using a centrifugal wheel atomizer at 45000 RPM. The collected powder is Example 11A.

After spray drying the samples were oven baked to complete acrylate based cross linking polymerization and encapsulate active with acrylate barrier which would be later difficult to breakdown in detergent solution. Powder Example 11A is baked at 110° C. for 30 mins, followed by 130° C. for 1 hr and at last 30 min. at 150° C. for the reaction to complete. Color of sample heated at 150° C. turned brown. Samples were collected after baking at each of the temperatures. These samples are labeled Example 11B.

The capsules are evaluated via the Detergent Dissolution Test. Samples baked at 110° C./30 minutes+130° C./1 hr show the best fragrance stability and release profile. The sample baked at 150° C. results in a strong odor that dominated, and does not express the full perfume palette.

Example 12

A Compilation of Microcapsule Examples, 15% Perfume in Slurry

The following tables summarize additional examples of microcapsules prepared using a variety of ingredients and under a variety of preparation conditions.

TABLE 12-1

Examples 12A-12P.

| Material | A | B | C | D | E | F | G | H | J | K | L | M | N | P |
|---|---|---|---|---|---|---|---|---|---|---|---|---|---|---|
| Perfume Oil | 23 | 23 | 23 | 23 | 23 | 23 | 23 | 23 | 23 | 23 | 23 | 23 | 23 | 23 |
| CN9302 | 5 | 5 | 5 | 5 | 5 | 5 | 5 | 5 | 5 | 5 | 5 | 5 | 5 | 5 |
| Vazo-67 | 1.2 | 1.2 | 1.2 | 1.2 | 1.2 | 1.2 | 1.2 | 1.2 | 1.2 | 1.2 | 1.2 | 1.2 | 1.2 | 1.2 |
| Urea | 0.8 | | | | | | | | | | | | | |
| Aniline | | 0.8 | | | | | | | | | | | | |
| Chitosan | | | 0.8 | | | | | | | | | | | |
| Melamine | | | | 0.8 | | | | | | | | | | |
| p-nitroaniline | | | | | 0.8 | | | | | | | | | |
| Guanidine. HCL | | | | | | 0.8 | | | | | | | | |
| Lysine. HCL | | | | | | | 0.8 | | | | | | | |
| Histidine. HCL | | | | | | | | 0.8 | | | | | | |
| Tryptophan. HCL | | | | | | | | | 0.8 | | | | | |
| 4-octyloxyaniline | | | | | | | | | | 0.8 | | | | |
| 4-piperizylaniline | | | | | | | | | | | 0.8 | | | |
| 4-aminobenzoic acid | | | | | | | | | | | | 0.8 | | |
| Cyanamide | | | | | | | | | | | | | 0.8 | |
| Procaine hydrochloride | | | | | | | | | | | | | | 0.8 |
| 5% Sokalan K90P Solution | 100 | 100 | 100 | 100 | 100 | 100 | 100 | 100 | 100 | 100 | 100 | 100 | 100 | 100 |
| Organic Base | 0.2 | 0.2 | 0.2 | 0.2 | 0.2 | 0.2 | 0.2 | 0.2 | 0.2 | 0.2 | 0.2 | 0.2 | 0.2 | 0.2 |
| N,N-methylenebisacrylamide | 1.85 | 1.85 | 1.85 | 1.85 | 1.85 | 1.85 | 1.85 | 1.85 | 1.85 | 1.85 | 1.85 | 1.85 | 1.85 | 1.85 |
| diacetone acrylamide | 1 | 1 | 1 | 1 | 1 | 1 | 1 | 1 | 1 | 1 | 1 | 1 | 1 | 1 |
| Room Temperature Reaction after amine addition | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs |
| Temperature Ramp Rate to 70 C. | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes |
| Hours of reaction at 70 C. | 5 hours | 5 hours | 5 hours | 5 hours | 5 hours | 5 hours | 5 hours | 5 hours | 5 hours | 5 hours | 5 hours | 5 hours | 5 hours | 5 hours |
| Temperature Ramp Rate to 90 C. | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes |
| Hours of reaction at 90 C. | 2 hours | 2 hours | 2 hours | 2 hours | 2 hours | 2 hours | 2 hours | 2 hours | 2 hours | 2 hours | 2 hours | 2 hours | 2 hours | 2 hours |
| Modified Starch | 0.3 | 0.3 | 0.3 | 0.3 | 0.3 | 0.3 | 0.3 | 0.3 | 0.3 | 0.3 | 0.3 | 0.3 | 0.3 | 0.3 |
| Silica | 0.3 | 0.3 | 0.3 | 0.3 | 0.3 | 0.3 | 0.3 | 0.3 | 0.3 | 0.3 | 0.3 | 0.3 | 0.3 | 0.3 |
| Observations (capsules? No capsules?) | capsules | capsules | capsules | capsules | capsules | capsules | capsules | capsules | capsules | capsules | capsules | capsules | capsules | capsules |
| Extra Water | 20 | 20 | 20 | 20 | 20 | 20 | 20 | 20 | 20 | 20 | 20 | 20 | 20 | 20 |
| % Perfume | 15.0% | 15.0% | 15.0% | 15.0% | 15.0% | 15.0% | 15.0% | 15.0% | 15.0% | 15.0% | 15.0% | 15.0% | 15.0% | 15.0% |

TABLE 12-2

Examples 12Q-12Z

| Material | Q | R | S | S1 | S2 | T | V | X | Y | Z |
|---|---|---|---|---|---|---|---|---|---|---|
| Perfume Oil | 23 | 23 | 23 | 23 | 23 | 10 | 13 | 23 | 35 | 60 |
| CN9302 | 5 | 5 | 5 | 5 | 5 | 10 | 5 | 5 | 5 | 2.7 |
| Vazo-67 | 1.2 | 1.2 | 1.2 | 1.2 | 1.2 | 1.4 | 1.4 | 1.4 | 1.4 | 0.9 |
| Urea | 0.8 | 0.8 | 0.8 | 0.8 | 0.8 | | | | | 0.8 |
| Aniline | | | | | | 1 | 0.5 | 0.5 | 0.5 | |
| 5% Sokalan K90P Solution | 100 | 100 | 100 | 100 | 100 | 100 | 100 | 100 | 100 | 220 |
| Organic Base | | | | | | 0.2 | 0.2 | 0.2 | 0.2 | 0.2 |
| N,N-methylenebisacrylamide | 1 | 1 | 1 | 1 | 1 | | | | | 0.9 |
| diacetone acrylamide | 1.85 | | | | | 3.7 | 1.85 | 1.85 | 1.85 | 1 |
| 2-(Acryloyloxy)ethyltrimethylammonium chloride | | 1.85 | | | | | | | | |
| [3-acrylamidopropyl)trimethyl ammonium chloride solution | | | 1.85 | 1.85 | | | | | | |
| Room Temperature Reaction after amine addition | 5 hrs | 5 hrs | 5 hrs | 5 hrs | 1.85 / 5 hrs | 5 hrs | 5 hrs | 5 hrs | 5 hrs | 5 hrs |
| Temperature Ramp Rate to 70 C. | 20 minutes | 20 minutes | 20 minutes | 20 minutes | 20 minutes | 20 minutes | 20 minutes | 20 minutes | 20 minutes | 20 minutes |
| Hours of reaction at 70 C. | 5 hours | 5 hours | 5 hours | 5 hours | 5 hours | 5 hours | 5 hours | 5 hours | 5 hours | 5 hours |
| Temperature Ramp Rate to 90 C. | 15 minutes | 15 minutes | 15 minutes | 15 minutes | 15 minutes | 15 minutes | 15 minutes | 15 minutes | 15 minutes | 15 minutes |
| Hours of reaction at 90 C. | 2 hours | 2 hours | 2 hours | 2 hours | 2 hours | 2 hours | 2 hours | 2 hours | 2 hours | 2 hours |
| Observations (capsules? No capsules?) | capsules | capsules | capsules | capsules | capsules | capsules | capsules | capsules | capsules | capsules |
| Extra Water | 22 | 22 | 22 | 22 | 22 | 0 | 0 | 20 | 90 | 114 |
| % Perfume | 14.9% | 14.9% | 14.9% | 15.0% | 15.0% | 7.9% | 10.7% | 15.1% | 15.0% | 15.0% |

TABLE 12-3

Examples 12AA-12AF and 12BH-12BL

| Material | AA | AB | AC | AD | AE | AF | BH | BJ | BK | BL |
|---|---|---|---|---|---|---|---|---|---|---|
| Perfume Oil | 23 | 23 | 23 | 23 | 23 | 23 | 60 | 60 | 60 | 60 |
| CN9302 | 5 | 5 | 5 | 5 | 5 | 5 | 2.7 | 2.7 | 2.7 | 2.7 |
| Vazo-67 | 1.4 | 1.4 | 1.4 | 1.4 | 1.4 | 1.4 | 0.6 | 0.3 | 0.9 | 0.9 |
| Vazo-87 | | | | | | | 0.3 | 0.3 | 0.3 | 0.3 |
| vazo-44 | | | | | | | | 0.3 | | 0.3 |
| Aniline | 0.8 | 0.8 | 0.8 | 0.8 | 0.8 | 0.8 | 0.8 | 0.8 | 0.8 | 0.8 |
| 5% Selvol 205S Solution | 100 | | | | | | | | | |
| 5% Sokalan K9OP Solution | | 100 | | | | | 220 | 220 | 220 | 220 |
| 5 wt % Ludox HS-30 | | | 100 | | | | | | | |
| 5% PVP-VA S630 | | | | 100 | | | | | | |
| 5% Selvol 540S | | | | | 100 | | | | | |
| 5% PVP-VA W735 | | | | | | 100 | | | | |
| 5% PVP-VA W635 | | | | | | | | | | |
| Organic Base | 0.2 | 0.2 | 0.2 | 0.2 | 0.2 | 0.2 | 0.2 | 0.2 | 0.2 | 0.2 |
| N,N-methylenebisacrylamide | 0.9 | 0.9 | 0.9 | 0.9 | 0.9 | 0.9 | 1.85 | 1.85 | 1.85 | 1.85 |
| Sartomer 206 | | | | | | | 1 | 1 | 1 | 1 |
| Room Temperature Reaction after amine addition | 5 hrs | 5 hrs | 5 hrs | 5 hrs | 5 hrs | 5 hrs | 5 | 5 | 5 | 5 |
| Temperature Ramp Rate to 70 C. | 20 minutes | 20 minutes | 20 minutes | 20 minutes | 20 minutes | 20 minutes | 20 minutes | 20 minutes | 20 minutes | 20 minutes |
| Hours of reaction at 70 C. | 5 hours | 5 hours | 5 hours | 5 hours | 5 hours | 5 hours | 2 | 2 | 2 | 2 |
| Temperature Ramp Rate to 90 C. | 15 minutes | 15 minutes | 15 minutes | 15 minutes | 15 minutes | 15 minutes | 15 minute | 15 minute | 15 minute | 15 minute |
| Hours of reaction at 90 C. | 2 hours | 2 hours | 2 hours | 2 hours | 2 hours | 2 hours | 2 hours | 2 hours | 2 hours | 2 hours |
| Observations (capsules? No capsules?) | capsules | capsules | capsules | capsules | capsules | capsules | capsules | capsules | capsules | capsules |
| Extra Water | 22 | 22 | 22 | 22 | 22 | 22 | 114 | 114 | 114 | 114 |
| % Perfume | 15.0% | 15.0% | 15.0% | 15.0% | 15.0% | 15.0% | 14.9% | 14.9% | 14.9% | 14.9% |

TABLE 12-4

Examples 12AG-12AZ

| Material | AG | AH | AJ | AK | AL | AM | AN | AP | AO | AR | AS | AT | AV | AW | AX | AY | AZ |
|---|---|---|---|---|---|---|---|---|---|---|---|---|---|---|---|---|---|
| Perfume Oil | 60 | 60 | 60 | 60 | 60 | 60 | 60 | 60 | 60 | 38.5 | 38.5 | 38.5 | 23 | 23 | 23 | 38.5 | 39 |
| CN9302 | 2.7 | 2.7 | 2.7 | 2.7 | 2.7 | 2.7 | 2.7 | 2.7 | 2.7 | 2.5 | 1.75 | 2.5 | 5 | 2.7 | 2.7 | 2.5 | 2.5 |
| Vazo-67 | 0.9 | 0.9 | 0.9 | 0.9 | 0.9 | 0.9 | 0.9 | 0.9 | 0.9 | 0.6 | 0.6 | 0.6 | 1.2 | 0.9 | 0.9 | 0.6 | 0.6 |
| Aniline | 0.8 | 0.8 | 0.8 | 0.8 | 0.8 | 0.8 | 0.8 | 0.8 | 0.8 | 0.5 | 0.5 | 0.5 | 0.5 | 0.8 | 0.8 | 0.5 | 0.5 |
| 5% Sokalan K90P Solution | 220 | 220 | 220 | 220 | 220 | 220 | 220 | 220 | 220 | 100 | 100 | 100 | 100 | 100 | 100 | 100 | 100 |
| Organic Base | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| N,N-methylene-bisacrylamide | 0.9 | 0.9 | 0.9 | 0.9 | 0.9 | 0.9 | 0.9 | 0.9 | 0.9 | | | | | 0.9 | 0.9 | | |
| Sartomer 206 | 1 | | | | | | | | | | | | | | | | |
| Sartomer 247 | | 1 | | | | | | | | | | | | | | | |
| Sartomer 256 | | | 1 | | | | | | | | | | | | | | |
| Sartomer 295 | | | | | | 3 | | | | | | | | | | | |
| CN294E | | | | | 2 | | 1 | | | | | | | | | | |
| Polyester Acrylate CN2304 | | | | | | | 1 | 1 | | | | | | | | | |
| Polyester Acrylate CN981 | | | | 1 | | | | | 1 | | | | | | | | |
| CN9010 | | | | | | | | | | 0.5 | | | | | | | |
| CN968 | | | | | | | | | | | 0.75 | | | | | | |
| CN9026 | | | | | | | | | | | | 0.5 | | | | | |
| | | | | | | | | | | | | | 1 | 2.3 | 2.3 | 1.25 | 1.25 |
| Room Temperature Reaction after amine addition | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs | 5 hrs |

TABLE 12-4-continued

Examples 12AG-12AZ

| Material | AG | AH | AJ | AK | AL | AM | AN | AP | AO | AR | AS | AT | AV | AW | AX | AY | AZ |
|---|---|---|---|---|---|---|---|---|---|---|---|---|---|---|---|---|---|
| Temperature Ramp Rate to 70 C. | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes | 20 minutes |
| Hours of reaction at 70 C. | 5 hours | 5 hours | 5 hours | 5 hours | 5 hours | 5 hours | 5 hours | 5 hours | 5 hours | 5 hours | 5 hours | 5 hours | 5 hours | 5 hours | 5 hours | 5 hours | 5 hours |
| Temperature Ramp Rate to 90 C. | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes | 15 minutes |
| Hours of reaction at 90 C. | 2 hours | 2 hours | 2 hours | 2 hours | 2 hours | 2 hours | 2 hours | 2 hours | 2 hours | 2 hours | 2 hours | 2 hours | 2 hours | 2 hours | 2 hours | 2 hours | 2 hours |
| Modified Starch | | | | | | | | | | | 0.3 | 0.3 | 0.3 | | | | |
| Silica | | | | | | | | | | | 0 | 0 | 0 | | | | |
| Observations (capsules? No capsules?) | capsules | capsules | capsules | capsules | capsules | capsules | capsules | capsules | capsules | no capsules | no capsules | no capsules | no capsules | capsules | capsules | capsules | capsules |
| Extra Water | 114 | 114 | 114 | 114 | 113 | 112 | 112 | 113 | 113 | 114 | 115 | 115 | 22 | 23 | 23 | 112 | 114 |
| % Perfume | 15.0% | 15.0% | 15.0% | 15.0% | 15.0% | 15.0% | 15.0% | 15.0% | 15.0% | 15.5% | 15.0% | 15.0% | 15.0% | 15.0% | 15.0% | 15.0% | 15.1% |

TABLE 12-5

Examples BA-BG.

| Material | BA | BC | BD | BE | BF | BG |
|---|---|---|---|---|---|---|
| Perfume Oil | 23 | 23 | 23 | 23 | 60 | 60 |
| CN9302 | 5 | 5 | 5 | 5 | 2.7 | 2.7 |
| Vazo-67 | 1.2 | 1.2 | 1.2 | 1.2 | 0.9 | 0.9 |
| Aniline | 0.8 | 0 | 0 | 0 | 0.8 | 0.8 |
| 5% Sokalan K90P Solution | 100 | 100 | 100 | 100 | 220 | 220 |
| Organic Base | 0.2 | 0.2 | 0.2 | 0.2 | 0.2 | 0.2 |
| N,N-methylenebisacrylamide | 1.85 | 1.85 | 1.85 | 1.85 | 1.85 | 1.85 |
| Sartomer 206 | 1 | 1 | 1 | 1 | 1 | 1 |
| Sartomer 247 | | | | | | 1 |
| Room Temperature Reaction after amine addition | 1 | 2 | 4 | 5 | 5 | 5 |
| Temperature Ramp Rate to 70 C. | 20 minutes | 20 minutes | 20 minutes | 20 minutes | 20 minutes | 20 minutes |
| Hours of reaction at 70 C. | 5 hours | 5 hours | 5 hours | 2 | 2 | 2 |
| Temperature Ramp Rate to 90 C. | 15 minutes | 15 minutes | 15 minutes | 15 minute | 15 minute | 15 minute |
| Hours of reaction at 90 C. | 2 hours | 2 hours | 2 hours | 2 hours | 2 hours | 2 hours |
| Observations (capsules? No capsules?) | capsules | capsules | capsules | capsules | capsules | capsules |
| Extra Water | 20 | 20 | 20 | 20 | 114 | 114 |
| % Perfume | 15.0% | 15.1% | 15.1% | 15.1% | 14.9% | 14.9% |

Example 13

Hair Conditioner

Selected microcapsules from the above examples are formulated into a leave-on-conditioner formulation as follows: to 98.0 grams of leave-on-conditioner (with a typical formulation given below) is added an appropriate amount of microcapsule slurry of Examples 8 and 9, to deliver an encapsulated oil usage level of 0.5 wt. %. The microcapsules are added on top of the conditioner formulation, then the contents are mixed at 1000 RPM for 1 minute.

A typical composition of a leave-on conditioner formulation is given in Table 12 below.

TABLE 13

Hair Condition Formulation

| Components | Ex. I (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |
| DTDMAC, C18(Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Others | |
| Preservatives | 0.40-0.60 |

Example 14

Shampoo

Selected microcapsules from the above examples are formulated into a rinse-off shampoo formulation as follows: to 90.0 grams of shampoo formulation is added an appropriate amount of microcapsule slurry of Examples 8 and 9, to deliver an encapsulated oil usage level of 0.5 wt. %. The microcapsules and water are added on top of the shampoo formulation, then the contents are mixed at 1850 RPM for 1 minute. Typical shampoo formulations are shown in Tables 14.1, 14.2 and 14.3 below.

TABLE 14.1

Shampoo Formulations of Examples 14A-14C.

| Ingredient | 14A | 14B | 14C |
|---|---|---|---|
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Fragrance Microcapsules | 1.2 | 1.2 | 1.2 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW - 500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

TABLE 14.2

Shampoo Formulations of Examples 14D-14F.

| Ingredient | 14D | 14E | 14F |
|---|---|---|---|
| Water | q.s. | q.s. | q.s. |
| Silicone A [1] | 1.0 | 0.5 | 0.5 |
| Cyclopentasiloxane [4] | — | 0.61 | 1.5 |
| Behenyl trimethyl ammonium chloride [5] | 2.25 | 2.25 | 2.25 |
| Isopropyl alcohol | 0.60 | 0.60 | 0.60 |
| Cetyl alcohol [6] | 1.86 | 1.86 | 1.86 |
| Stearyl alcohol [7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/Methylisothiazolinone [8] | 0.0005 | 0.0005 | 0.0005 |
| Panthenol [9] | 0.10 | 0.10 | 0.10 |
| Panthenyl ethyl ether [10] | 0.05 | 0.05 | 0.05 |
| Fragrance | 0.35 | 0.35 | 0.35 |
| Fragrance Microcapsules | 1.2 | 1.2 | 1.2 |

[1] Glycidol Silicone
[4] Cyclopentasiloxane: SF1202 available from Momentive Performance Chemicals
[5] Behenyl trimethyl ammonium chloride/Isopropyl alcohol: Genamin TM KMP available from Clariant
[6] Cetyl alcohol: Konol TM series available from Shin Nihon Rika
[7] Stearyl alcohol: Konol TM series available from Shin Nihon Rika
[8] Methylchloroisothiazolinone/Methylisothiazolinone: Kathon TM CG available from Rohm & Haas
[9] Panthenol: Available from Roche
[10] Panthenyl ethyl ether: Available from Roche

TABLE 14.3

Shampoo Formulations of Examples 14G and 14H

| Ingredient | 14G | 14H |
|---|---|---|
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

(1) Jaguar C17 available from Rhodia
(2) N-Hance 3269 (with Mol. W. of ~500,000 and 0.8 meq/g) available from Aqulaon/Hercules
(3) Viscasil 330M available from General Electric Silicones
(4) Gel Networks; See composition in Table 16 below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

TABLE 14.4

Gel Network Composition

| Ingredient | Wt. % |
|---|---|
| Water | 86.14% |
| Cetyl Alcohol | 3.46% |
| Stearyl Alcohol | 6.44% |
| Sodium laureth-3 sulfate (28% Active) | 3.93% |
| 5-Chloro-2-methyl-4-isothiazolin-3-one, Kathon CG | 0.03% |

Example 15

Lotion

For the examples shown in Table 15 below, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

TABLE 15

Lotion Formulations (Examples 15A-15C).

| Ingredient/Property | 15A | 15B | 15C |
|---|---|---|---|
| PHASE A | | | |
| DC-9040 [1] | 8.60 | 3.00 | 5.00 |
| Dimethicone | 4.09 | 4.00 | 4.00 |
| Polymethylsilsesquioxane [2] | 4.09 | 4.00 | 4.00 |
| Cyclomethicone | 11.43 | 0.50 | 11.33 |
| KSG-210 [3] | 5.37 | 5.25 | 5.40 |
| Polyethylene wax [4] | 3.54 | | 2.05 |
| DC-2503 Cosmetic Wax [5] | 7.08 | 10.00 | 3.77 |
| Hydrophobic TiO$_2$ | | | 0.50 |
| Iron oxide coated Mica | | | 0.65 |
| TiO$_2$ Coated Mica | 1.00 | 1.00 | |
| Fragrance Microcapsules of Example 8, 9, 12 | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate [6] | 0.10 | 0.10 | 0.10 |
| Niacinamide [7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1] 12.5% Dimethicone Crosspolymer in Cyclopentasiloxane. Available from Dow Corning.
[2] E.g., TOSPEAR 145A or TOSPEARL 2000. Available from GE Toshiba Silicon.
[3] 25% Dimethicone PEG-10/15 Crosspolymer in Dimethicone. Available from Shin-Etsu.
[4] JEENATE 3H polyethylene wax from Jeen.
[5] Stearyl Dimethicone. Available from Dow Corning.
[6] Hexamidine diisethionate, available from Laboratoires Serobiologiques.
[7] Additionally or alternatively, the composition may comprise one or more other skin care actives, their salts and derivatives, as disclosed herein, in amounts also disclosed herein as would be deemed suitable by one of skill in the art.

Example 16

Antiperspirant/Deodorant

Example 16A of Table 16.1 below can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with a suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

TABLE 16.1

Antiperspirant/Deodorant Formulation (Example 16A).

| Ingredient | Example 16A |
|---|---|
| Part I: Partial Continuous Phase | |
| Hexamethyldisiloxane[1] | QS |
| DC5200[2] | 1.20 |
| Fragrance | 0.35 |
| Fragrance Capsules of Examples 11A, 11B | 1.00 |
| Part II: Disperse Phase | |
| ACH (40% solution)[4] | 40.00 |
| propylene glycol | 5.00 |
| Water | 12.30 |
| Part III: Structurant Plus Remainder of Continuous Phase | |
| FINSOLVE TN | 6.50 |

QS - indicates that this material is used to bring the total to 100%.
[1] DC 246 fluid from Dow Corning
[2] from Dow Corning
3 Standard aluminum chlorohydrate solution Examples 16B to 16E of Table 16.2 below can be made as follows: all ingredients except the fragrance, and fragrance capsules are combined in a suitable container and heated to about 85° C. to form a homogenous liquid. The solution is then cooled to about 62° C. and then the fragrance, and fragrance microcapsules are added. The mixture is then poured into an appropriate container and allowed to solidify up cooling to ambient temperature.

Example 16F of Table 16.2 can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

TABLE 16.2

Antiperspirant/Deodorant Formulations

| | Example | | | | |
|---|---|---|---|---|---|
| Ingredient | 16B | 16C | 16D | 16E | 16F |
| Product Form | Solid Deodor-ant | Solid Deodor-ant | Solid Deodor-ant | Solid Deodor-ant | Deodor-ant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragramce | 0.5 | 0.5 | 0.5 | 0.5 | 0.5 |
| Fragrance capsules of Example 11A, 11B | 1.0 | 1.0 | 1.0 | 1.0 | 0.5 |
| Propellant (1,1 difluoroethane) | | | | | 40 |

QS - indicates that this material is used to bring the total to 100%.

Example 17

Rinse-Off Conditioner

The conditioning compositions of Examples 17A through 17F of Table 17 are prepared as follows: cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of Example 17B of Table 17 is prepared as follows: cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

TABLE 20

Rinse-Off Conditioner Formulations (Examples 17A-17F).

| | Example | | | | | |
|---|---|---|---|---|---|---|
| Ingredient | 17A | 17B | 17C | 17D | 17E | 17F[3] |
| Premix | | | | | | |
| Aminosilicone-1 [1] | 0.50 | 0.50 | | | | |
| Aminosilicone-2 [2] | | | 0.50 | 0.50 | 0.50 | |
| PDMS | | | | | | 0.50 |
| Fragrance microcapsules of Example 8 or 9 or 12 | . . . | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |

TABLE 20-continued

Rinse-Off Conditioner Formulations (Examples 17A-17F).

| Ingredient | 17A | 17B | 17C | 17D | 17E | 17F[3] |
|---|---|---|---|---|---|---|
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

[1] Aminosilicone-1 (AMD): having an amine content of 0.12-0.15 m mol/g and a viscosity of 3,000-8,000 mPa · s, which is water insoluble
[2] Aminosilicone-2 (TAS): having an amine content of 0.04-0.06 m mol/g and a viscosity of 10,000-16,000 mPa · s, which is water insoluble
[3] Comparative example with PDMS instead of amino silicone

Example 18

Body Cleansing Composition

The body cleaning compositions of Examples 18A-18C are prepared as follows.

The cleansing phase composition is prepared by adding surfactants, guars, and Stabylen 30 to water. Sodium chloride is then added to the mixture to thicken the cleansing phase composition. Preservatives and chelants are added to the formulation. Finally, perfume is added to the suspension.

The Benefit phase composition is prepared by mixing petrolatum and mineral oil to make a homogeneous mixture. Fragrance microcapsules are added to the suspension. Finally, the cleansing phase (e.g. surfactant phase) and benefit phase are mixed in different ratios to yield the body cleansing composition.

TABLE 18

Body Cleansing Composition Formulations (Examples 18A-18C).

| Ingredient | 18A | 18B | 18C |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition | | | |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules of Example 8 or 9 or 12 | 10 | 10 | 10 |
| III: Surfactant Phase:Benefit Phase Blending Ratio | 50:50 | 90:10 | 90:10 |

Example 19

Fabric Softening Product

Non-limiting examples of product formulations containing purified perfume microcapsules of the aforementioned examples are summarized in the following table.

TABLE 19

Fabric Softening Product Formulations (Examples 19A-19J).

| Ingredient | 19A | 19B | 19C | 19D | 19E | 19F | 19G | 19H | 19I | 19J |
|---|---|---|---|---|---|---|---|---|---|---|
| FSA [a] | 14 | 16.47 | 14 | 12 | 12 | 16.47 | 3.00 | 6.5 | 5 | 5 |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250[j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |

TABLE 19-continued

Fabric Softening Product Formulations (Examples 19A-19J).

| Ingredient | 19A | 19B | 19C | 19D | 19E | 19F | 19G | 19H | 19I | 19J |
|---|---|---|---|---|---|---|---|---|---|---|
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant$^l$ | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

$^a$ N,N-di(tallowoyloxyethyl)-N,N-dimethylammonium chloride.
$^f$ Copolymer of ethylene oxide and terephthalate having the formula described in U.S. Pat. No. 5,574,179 at col.15, lines 1-5, wherein each X is methyl, each n is 40, u is 4, each R1 is essentially 1,4-phenylene moieties, each R2 is essentially ethylene, 1,2-propylene moieties, or mixtures thereof.
$^g$ SE39 from Wacker
$^h$ Diethylenetriaminepentaacetic acid.
$^i$ KATHON CG available from Rohm and Haas Co. "PPM" is "parts per million."
$^j$ Gluteraldehyde
$^k$ Silicone antifoam agent available from Dow Corning Corp. under the trade name DC2310.
$^l$ Hydrophobically-modified ethoxylated urethane available from Rohm and Haas under the tradename Aculyn™ 44.
*Suitable microcapsules provided in Examples 8 or 9 or 12. (Percent active relates to the core content of the microcapsule)

Example 20

Dry Laundry Formulations

Non-limiting examples of product formulations containing purified perfume microcapsules of the aforementioned examples are summarized in the following table.

TABLE 20

Dry Laundry Formulations (Examples 20A-20G)

| Ingredient | 20A | 20B | 20C | 20D | 20E | 20F | 20G |
|---|---|---|---|---|---|---|---|
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | QS | QS | QS | QS | QS | QS | QS |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt. % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt. % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules (Example 11A, 11B) | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

% w/w granular laundry detergent composition

QS - as used herein indicates that this material is used to bring the total to 100%.

Example 21

Liquid Laundry Formulations (HDLs)

Non-limiting examples of product formulations containing purified perfume microcapsules of the aforementioned examples are summarized in Tables 21.1, 21.2 and 21.3 below.

TABLE 21.1

Liquid Laundry Formulations (HDLs)

| Ingredient | 21A | 21B | 21C | 21D | 21E | 21F |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine pentamethylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules of Example 8 or 9 or 12 | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

TABLE 21.2

Liquid Laundry Detergent Formulations

| Ingredient | 21G | 21H | 21I | 21J |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | 1.0 | |
| Dye | 0.002 | 0.002 | 0.002 | 0.002 |
| Opacifier (Styrene Acrylate based) | 0.1 | | | |
| Bentonite Softening Clay | | 1.0 | | |
| Polyquaternium 10 - Cationic hydroxyl ethyl cellulose | 1.0 | | 1.0 | 1.0 |
| PP-5495 (silicone ex Dow Corning Corporation, Midland, MI) | | 1.0 | | |
| DC 1664 (silicone ex Dow Corning Corporation, Midland, MI) | | | 1.0 | |
| Perfume micro capsules (expressed as perfume oil) of Example 8 or 9 or 12 | 0.8 | 0.5 | 1.0 | 0.7 |
| Perfume | 0.7 | 0.55 | 1.00 | 1.00 |
| Poly Ethylene Imine MW 25000 | 0.1 | | | |
| Water | Up to 100 | Up to 100 | Up to 100 | Up to 100 |

TABLE 21.3

Liquid Laundry Detergent Formulations.

| Ingredient | 21K | 21L | 21M |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) of Example 8 or 9 or 12 | 1.6 | 1.5 | 1.4 |
| Perfume | 1.2 | 1.6 | 1.0 |
| Form. Phenyl Boronic Acid | | | Present |
| Water** | Up to 100 | Up to 100 | Up to 100 |

**Low water liquid detergent in Polyvinylalcohol unidose/sachet

TABLE 22

Liquid and Gel Detergent Formulations (% by Weight)

| Ingredient | 22A | 22B | 22C |
|---|---|---|---|
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Example 8 or 9 or 12 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 s$^{-1}$, cps | 2700 | 400 | 300 |

Example 22

Liquid and Gel Detergents

Non-limiting examples of product formulations containing purified perfume microcapsules of the aforementioned examples are summarized in Table 22 below.

Example 23

Liquid Unit Dose

The following are examples of unit dosage forms wherein the liquid composition is enclosed within a PVA film. The preferred film used in the present examples is Monosol M8630 76 μm thickness.

TABLE 23

Unit Dose Laundry Cleaner

| | 23A 3 compartments | | | 23B 2 compartments | | 23C 3 compartments | | |
|---|---|---|---|---|---|---|---|---|
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| C$_{12-14}$ alkyl 7-ethoxylate | 17.0 | 17.0 | 17.0 | | 17.0 | 17.0 | 15 | 10 |
| C$_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| C$_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |

TABLE 23-continued

Unit Dose Laundry Cleaner

| | Example | | | | | | | |
|---|---|---|---|---|---|---|---|---|
| | 23A 3 compartments | | | 23B 2 compartments | | 23C 3 compartments | | |
| Compartment # | 42 | 43 | 44 | 45 | 46 | 47 | 48 | 49 |
| Dosage (g) | 34.0 | 3.5 | 3.5 | 30.0 | 5.0 | 25.0 | 1.5 | 4.0 |
| Ingredients | Weight % | | | | | | | |
| Hydroxyethane diphosphonic acid | 0.6 | 0.6 | 0.6 | 0.5 | | | 2.2 | |
| Ethylene diamine tetra(methylene phosphonic) acid | | | | | 0.4 | | | |
| Brightener | 0.2 | 0.2 | 0.2 | 0.3 | | 0.3 | | |
| Microcapsules Example 8 or 9 or 12 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, ...) | 2.0 | 2.0 | 2.0 | 4.0 | 1.5 | 2.2 | 2.2 | 2.0 |
| Buffers (sodium carbonate, monoethanolamine) [2] | To pH 8.0 for liquids To RA > 5.0 for powders | | | | | | | |
| Solvents (1,2 propanediol, ethanol), sodium sulfate | To 100p | | | | | | | |

[1] Polyethylenimine (MW = 600) with 20 ethoxylate groups per —NH.
[2] RA = Reserve Alkalinity (g NaOH/dose)

Example 24

Environmental Biodegradability

Microcapsules of Example 4F were evaluated for environmental biodegradability by adapting the OCDE/OECD 301D Closed Bottle Test method. 3 liters of water from a fresh river source (Lehigh River, Sand Island Access Point, Bethlehem, Pa.) was filtered through a Whatman 597 (catalog 10311808) filter using a Buchner funnel assembly. The following mineral solutions of Table 29 were made:

TABLE 24

Mineral Oil Solutions

| Mineral Solution ID | Ingredient | Formula | Mass (g) |
|---|---|---|---|
| A | Potassium dihydrogen orthophosphate | $KH_2PO_4$ | 8.50 |
| | Dipostassium hydrogen orthophosphate | $K_2HPO_4$ | 21.75 |
| | Disodium hydrogen orthophosphate dihydrate | $Na_2HPO_4$—$2H_2O$ | 33.40 |
| | Ammonium chloride Dissolve in water and bring to 1 L. pH to 7.4 | $NH_4Cl$ | 0.50 |
| B | Calcium Chloride anhydrous OR | $CaCl_2$ | 27.50 |
| | Calcium Chloride dihydrate Dissolve in water and bring to 1 L. | $CaCl_2$—$2H_2O$ | 36.40 |
| C | Magnesium sulfate heptahydrate Dissolve in water and bring to 1 L. | $MgSO_4$—$7H_2O$ | 22.50 |
| D | Iron (III) chloride hexahydrate Dissolve in water and bring to 1 L. | $FeCl_3$—$6H_2O$ | 0.25 |

To 996 mL of the filtered water solution, add 1 mL each of mineral solutions A, B, C, and D. Prepare approximately 500 mL solutions containing the particles to be tested. Fill BOD bottles (500 mL capacity) just past the neck of the bottle. Insert stopper. Store BOD bottles in the dark. Use dissolved oxygen meter (YSI 5000), and YSI5905 Dissolved Oxygen meter probe to measure oxygen at specific time points.

While the invention has been described in detail and with reference to specific examples thereof, it will be apparent to one skilled in the art that various changes and modifications can be made therein without departing from the spirit and scope thereof.

What is claimed is:

1. A composition comprising controlled release particles which is an aqueous suspension of the controlled released particles, wherein each of the controlled release particles comprises:
    (a) a core comprising at least one hydrophobic active ingredient; and
    (b) a wall surrounding the core and comprising:
        (i) an outer layer comprising a copolymer of polyacrylamide and polyacrylate;
        (ii) an intermediate layer under the outer layer and comprising a polyurea;
        (iii) an inner layer under the intermediate layer and comprising an acrylate copolymer; and optionally
        (iv) an optional outer layer above the outer layer and comprising a quaternary amine containing moiety,
    wherein the acrylate copolymer comprises an acrylate of a urethane-acrylate oligomer containing both acrylate and isocyanate functionalities of a mixture from which the composition is formed, and the polyurea comprises an isocyanate of the urethane-acrylate oligomer containing both acrylate and isocyanate functionalities,
    wherein the inner layer is a mesh and the controlled release particles are effective to retain the at least one hydrophobic active ingredient upon exposure to water and effective to release the at least one hydrophobic active ingredient in response to friction, and
    wherein the controlled release particles are formed by a one-pot synthesis method from the mixture comprising 18-40 wt. % of the at least one hydrophobic active ingredient, 0.55-9.3 wt. % of the urethane-acrylate oligomer, 0.15-2.6 wt. % of an amine, 0.2-3 wt. % of at least one acrylamide, 0.2-3.8 wt. % of at least one initiator, 0.2-3.2 wt. % of at least one water dispersable acrylate, 1.5-8.6 wt. % of a water soluble emulsifier and 50-56 wt. % water.

2. The composition of claim 1, wherein the at least one hydrophobic active ingredient is at least one member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

3. The composition of claim 1, wherein the urethane-acrylate oligomer comprises acrylate and isocyanate functionalities, an isocyanate content from about 5 wt. % to about 15 wt. %, and an acrylate content from about 20 wt. % to about 50 wt. %.

4. The composition of claim 1, wherein the at least one water dispersible acrylate is a member selected from the group consisting of allyl methacrylate, triethylene glycol dimethacrylate, ethylene glycol dimethacrylate, diethylene glycol dimethacrylate, aliphatic urethane diacrylates, aromatic urethane diacrylates, difunctional urethane acrylates, ethoxylated aliphatic difunctional urethane methacrylates, aliphatic urethane dimethacrylates, aromatic urethane dimethacrylates, epoxy acrylates, epoxymethacrylates, tetraethylene glycol dimethacrylate, polyethylene glycol dimethacrylate, 1.3 butylene glycol diacrylate, 1,4-butanediol dimethacrylate, 1,4-butaneidiol diacrylate, diethylene glycol diacrylate, 1.6 hexanediol diacrylate, 1.6 hexanediol dimethacrylate, neopentylglycol diacrylate, polyethylene glycol diacrylate, tetraethylene glycol diacrylate, tri ethylene glycol diacrylate, 1.3 butylene glycol dimethacrylate, tripropylene glycol diacrylate, ethoxylated bisphenol diacrylate, ethoxylated bisphenol dimethylacrylate, dipropylene glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, ethoxylated trimethylolpropane triacrylate, propoxylated trimethylolpropane triacrylate, propoxylated glyceryl triacrylate, ditrimethylol propane tetraacrylate, dipentaerythritol pentaacrylate, and ethoxylated pentaerythritol tetraacrylate.

5. The composition of claim 1, wherein the amine is a member selected from the group consisting of lysine hydrochloride, urea, tryptophan hydrochloride, guanidine hydrochloride, aniline, cyanamide, 4-aminobenzoic acid, ethylenediamine, diethylenetriamine, guanidine and Girard's reagent.

6. The composition of claim 1, wherein the at least one acrylamide is an alkylidene-bis-acrylamide where the alkylidene group has up to four carbon atoms.

7. The composition of claim 1, wherein the at least one initiator used for polymerization is a member selected from the group consisting of peroxide, dialkyl peroxide, alkyl peroxide, peroxyester, peroxycarbonate, peroxyketone, peroxydicarbonate, 2,2'-azobis (isobutylnitrile), 2,2'-azobis (2,4-dimethylpentanenitrile), 2,2'-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1-azobis(cyanocyclohexane), benzoyl peroxide, decanoyl peroxide, lauroyl peroxide, benzoyl peroxide, di(n-propyl) peroxydicarbonate, di(sec-butyl)peroxydicarbonate, di(2-ethylhexyl)peroxydicarbonate, 1,1-dimethyl-3-hydroxybutyl peroxyneodecanoate, C-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di t-amyl peroxide, 2,5-dimethyl-2,5-di-(t-butylperoxy) hexyne-3, cumene hydroperoxide, 1,1-di-(t-butylperoxy)-3, 3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate and ethyl 3,3-di-(t-amylperoxy)-butyrate.

8. The composition of claim 1, wherein the emulsifier is selected from the group consisting of palmitamidopropyltrimonium chloride, distearyl dimonium chloride, cetyltrimethy lammonium chloride, quaternary ammonium compounds, fatty amines, aliphatic ammonium halides, alkyldimethyl benzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethylaminoethyl methacrylate), poly(acrylamide-co-diallyldimethylammonium chloride), poly(allylamine), polybis(2-chloroethyl)ether-alt-1,3-bis(3-(dimethylamino)propylurea quaternized, poly(dimethylamine-co-epichlorohydrin-co-ethylenediamine), polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, partially hydrolyzed polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), polyvinyl alcohol-co-ethylene, polyvinyl pyrrolidone, copolymers of polyvinhyl pyrrolidone, vinyl acetate and gum arabic.

9. The composition of claim 1, wherein the controlled release particles have a diameter from 0.1 microns to less than 200 microns.

10. The composition of claim 1, wherein at least 75% of the controlled release particles have a fracture strength of from about 0.2 MPa to about 30 MPa.

11. The composition of claim 1, which is used in forming a powdered food product, a fluid food product, a powdered nutritional supplement, a fluid nutritional supplement, a fluid fabric enhancer, a solid fabric enhancer, a fluid shampoo, a solid shampoo, a hair conditioner, a body wash, a solid antiperspirant, a fluid antiperspirant, a solid deodorant, a fluid deodorant, a fluid detergent, a solid detergent, a fluid hard surface cleaner, a solid hard surface cleaner, a fluid fabric refresher spray, a diaper, an air freshening product, a nutraceutical supplement, a controlled release fertilizer, a controlled release insecticide, a controlled release dye or a unit dose detergent comprising a detergent and the controlled release particles in a water soluble film.

12. The composition of claim 11, further comprising at least one suspension agent to suspend the controlled release particles, wherein the at least one suspension agent is selected from the group consisting of polyacrylates, polymethacrylates, polycarboxylates, pectin, alginate, gum arabic, carrageenan, gellan gum, xanthan gum, guar gum, gellan gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

13. The composition of claim 12, wherein the at least one suspension agent has a high shear viscosity at, 20 sec$^{-1}$ shear rate and at 21° C., of from 50 to 3000 cps and a low shear viscosity, at 0.5 sec$^{-1}$ shear rate at 21° C., of greater than 1000 cps.

14. The composition of claim 1, wherein the at least one hydrophobic active ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

15. The composition of claim 1, which has an Environmental Biodegradability greater than about 50% wherein the Environmental Biodegradability testing is carried out according to protocol OECD 30ID.

16. A method for preparing the composition of claim 1, said method comprising the steps of:
  (a) preparing a hydrophobic oil phase comprising the at least one hydrophobic active ingredient, the at least one urethane-acrylate oligomer, at least one acrylamide, at least one initiator and at least one water dispersible acrylate;
  (b) heating the hydrophobic oil phase to provide a homogeneous hydrophobic solution;
  (c) preparing an aqueous phase comprising water and a water soluble emulsifier;
  (d) combining the homogeneous hydrophobic phase and the aqueous phase with agitation conditions to provide a mixture containing droplets of a predetermined particle size;
  (e) adding to the mixture an amount of an amine, wherein a portion of the amount of the amine is optionally added to the aqueous phase before the combining step;
  adjusting a pH of the mixture of step (e) to at least about 8 to about 11 using an organic base;
  (g) maintaining agitation of the mixture of step (f) for a period of at least about 1 hour to about 10 hours at a temperature less than 40° C.;
  (h) adding an additional amount of the at least one acrylamide and an additional amount of the at least one initiator to the mixture of step (g);
  (i) heating the mixture of step (h) to about 70° C. to about 99° C. for a duration of about 1 hour to about 16 hours; and
  (j) cooling the mixture of step (i) to room temperature to provide the composition,
  wherein the method is conducted as a one-pot synthesis.

17. The method of claim 16, further comprising the step of adding suspending agents to the mixture of step (j) to minimize phase separation of the controlled release particles.

* * * * *